US012570694B2

(12) United States Patent
Expósito Tarrés et al.

(10) Patent No.: US 12,570,694 B2
(45) **Date of Patent: *Mar. 10, 2026**

(54) PEPTIDES AND PHARMACEUTICAL, NUTRACEUTICAL OR VETERINARY COMPOSITIONS FOR HAIR LOSS PREVENTION AND/OR TREATMENT

(71) Applicant: VYTRUS BIOTECH, S.L., Terrassa (ES)

(72) Inventors: Oscar Expósito Tarrés, Terrassa (ES); Albert Jané Font, Terrassa (ES); Sara Laplana Lasierra, Terrassa (ES); Maria Mas Duarte, Terrassa (ES); Tarik Ruiz Medina, Terrassa (ES); Ana Gallego Palacios, Terrassa (ES); Ana Belen Sabater Jara, Terrassa (ES)

(73) Assignee: VYTRUS BIOTECH, S.L., Terrassa (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/944,998

(22) Filed: Sep. 14, 2022

(65) Prior Publication Data

US 2023/0115426 A1     Apr. 13, 2023

Related U.S. Application Data

(63) Continuation of application No. 16/092,203, filed as application No. PCT/EP2017/057711 on Mar. 31, 2017, now Pat. No. 11,466,052.

(30) Foreign Application Priority Data

Apr. 11, 2016    (EP) ..................................... 16164645

(51) Int. Cl.
| | |
|---|---|
| *C07K 7/06* | (2006.01) |
| *A23L 33/15* | (2016.01) |
| *A23L 33/16* | (2016.01) |
| *A23L 33/175* | (2016.01) |
| *A23L 33/18* | (2016.01) |
| *A61K 31/047* | (2006.01) |
| *A61K 31/194* | (2006.01) |
| *A61K 31/197* | (2006.01) |
| *A61K 31/198* | (2006.01) |
| *A61K 31/375* | (2006.01) |
| *A61K 31/401* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/519* | (2006.01) |

(Continued)

(52) U.S. Cl.
CPC ................ *C07K 7/06* (2013.01); *A23L 33/15* (2016.08); *A23L 33/16* (2016.08); *A23L 33/175* (2016.08); *A23L 33/18* (2016.08);

*A61K 31/047* (2013.01); *A61K 31/194* (2013.01); *A61K 31/197* (2013.01); *A61K 31/198* (2013.01); *A61K 31/375* (2013.01); *A61K 31/401* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/675* (2013.01); *A61K 31/7076* (2013.01); *A61K 33/06* (2013.01); *A61K 33/14* (2013.01); *A61K 33/26* (2013.01); *A61K 33/30* (2013.01); *A61K 33/34* (2013.01); *A61K 36/9066* (2013.01); *A61K 38/07* (2013.01); *A61K 38/08* (2013.01); *A61K 45/06* (2013.01); *A61P 17/14* (2018.01); *C07K 5/10* (2013.01); *C07K 5/1016* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,139,619 A | 2/1979 | Chidsey, III |
| 4,596,812 A | 6/1986 | Charles, III et al. |

(Continued)

FOREIGN PATENT DOCUMENTS

| | | |
|---|---|---|
| CN | 103976908 | 8/2014 |
| DE | 19817177 | 10/1999 |

(Continued)

OTHER PUBLICATIONS

Cleveland Clinic (https://my.clevelandclinic.org/health/diseases/21753-hair-loss accessed Aug. 11, 2023).*

(Continued)

*Primary Examiner* — Lianko G Garyu
*Assistant Examiner* — Tara L Martinez
(74) *Attorney, Agent, or Firm* — Squire Patton Boggs (US) LLP

(57) ABSTRACT

Present invention discloses particular peptide sequences of formula (I);

$$(R^1)_{(m)}\text{-}Xaa_1IXaa_2T(Q)_{(p)}(R^2)_{(n)} \qquad \text{(I) (SEQ ID NO: 1)};$$

wherein $R^1$, m, p, n, $Xaa_1$, $Xaa_2$, and $R^2$ have particular meanings, or pharmaceutically or veterinary acceptable salts of these peptides that are effective in the prevention and/or treatment of mammal hair loss.

Invention also relates to particular topical pharmaceutical, nutraceutical or veterinary compositions with the peptides of formula (I).

8 Claims, 17 Drawing Sheets

Specification includes a Sequence Listing.

(51) Int. Cl.

| | | |
|---|---|---|
| *A61K 31/525* | (2006.01) |
| *A61K 31/675* | (2006.01) |
| *A61K 31/7076* | (2006.01) |
| *A61K 33/06* | (2006.01) |
| *A61K 33/14* | (2006.01) |
| *A61K 33/26* | (2006.01) |
| *A61K 33/30* | (2006.01) |
| *A61K 33/34* | (2006.01) |
| *A61K 36/9066* | (2006.01) |
| *A61K 38/07* | (2006.01) |
| *A61K 38/08* | (2019.01) |
| *A61K 45/06* | (2006.01) |
| *A61P 17/14* | (2006.01) |
| *C07K 5/10* | (2006.01) |
| *C07K 5/107* | (2006.01) |

(56) References Cited

U.S. PATENT DOCUMENTS

| | | |
|---|---|---|
| 6,281,241 B1 | 8/2001 | Elsner |
| 2014/0072619 A1 | 3/2014 | Blum et al. |
| 2015/0359830 A1 | 12/2015 | Stottlemyre et al. |

FOREIGN PATENT DOCUMENTS

| | | |
|---|---|---|
| EP | 1243654 A1 | 9/2002 |
| EP | 1498475 A1 | 1/2005 |
| EP | 2436759 A2 | 4/2012 |
| EP | 2687592 A1 | 1/2014 |
| EP | 2708596 A1 | 3/2014 |
| FR | 2854328 A1 | 11/2004 |
| WO | WO 2006/087759 | 8/2006 |
| WO | WO 2007/113851 | 10/2007 |
| WO | WO 2012/017067 | 2/2012 |
| WO | WO 2012/130783 A2 | 10/2012 |
| WO | WO 2016/166047 | 10/2016 |

OTHER PUBLICATIONS

Basmanav et al. ("Recent advances in the genetics of alopecia areata" De Gruyter Apr. 5, 2023).*

Choi, Jae-Hoon, et al: Antitumor activity of cell suspension culture of green tea seed (*Camellia sinensis* L.), Biotechnology and Bioprocess Engineering, Sep. 1, 2006, vol. 11, pp. 396-401.

Czyzewicz, Nathan, et al: "Message in a bottle: small signalling peptide outputs during growth and development", Journal of Experimental Botany, Sep. 7, 2013, vol. 654, No. 17, pp. 5281-5296.

Dimri, Goberdhan P., et al: "A biomarker that identifies senescent human cells in culture and in aging skin in vivo", Proc. Natl. Acad. Sci. USA, Sep. 1995, vol. 92, pp. 9363-9367.

Ryan, Clarence A., et al.: "Polypeptide Hormones", The Plant Cell Supplement May 2002, pp. S251-S264.

DermaScope: https://www.dermascope.com/ingredients/mineral-skin-care; May 2011.

International Search Report and Written Opinion mailed May 29, 2017 for PCT Application No. PCT/EP2017/057711, 19 pages.

Hellwig, et al. "Plant cell cultures for the production of recombinant proteins", Nature Biotechnology, Gale Group Inc, 2004, vol. 22, No. 11, pp. 1414-1420, Nov. 2004.

Matsubayashi, et al., "Phytosulfokine, sulphated peptides that induce the proliferation of single mesophyll cells of *Asparagus officinalis* L.", Proc. Natl. Acad. Sci. 1996, vol. No. 93, pp. 7623-7627, Jul. 1996.

Merrell, "The importance of minerals in the long term health of humans", Jost Chemical Co.; Feb. 26, 2016.

Park, "Role of micronutrients in skin health and function", Biomol Ther (Seoul); May 2015; vol. 23(3), pp. 207-217.

Pumthong, et al. "Curcuma aeruginosa, a novel botanically derived 5a-reductase inhibitor in the treatment of male-pattern baldness: a multicenter, randomized, double-blind, placebo-controlled study", Journal of Dermatological Treatment. 2012; vol. No. 23, pp. 385-392, Jul. 2011.

SK Bioland: https://www.skibioland.com/en/raw/makeup_0202.jsp; Oct. 27, 2015.

Vitamins in Cosmetics, Medical Beauty Forum 2011; pp. 14-16.

* cited by examiner

A

B

C

Relative cell viability of keratinocytes

Relative cell viability of keratinocytes

PEPTIDES AND PHARMACEUTICAL, NUTRACEUTICAL OR VETERINARY COMPOSITIONS FOR HAIR LOSS PREVENTION AND/OR TREATMENT

CROSS-REFERENCE TO RELATED APPLICATIONS

This application is a continuation of U.S. application Ser. No. 16/092,203, filed Oct. 8, 2018, which is a national-stage filing under 35 USC 371 (c) of International Application No. PCT/EP2017/057711, filed Mar. 31, 2017, which claims the benefit of European Patent Application EP 16164645.0 filed on Apr. 11, 2016. The entire contents of these applications are incorporated by reference herein in their entirety for all purposes.

REFERENCE TO ELECTRONIC SEQUENCE LISTING

This application contains a sequence listing which has been submitted electronically in .XML format and is hereby incorporated by reference in its entirety. Said .XML copy, created on Nov. 10, 2022, is named "108663_00315_ST26.xml" and is 30,880 bytes in size which is a copy of the sequence listing as filed in PCT/EP2017/057711. The sequence listing contained in this .XML file is part of the specification and is hereby incorporated by reference herein in its entirety.

Present invention relates to the field of hair loss treatment of any cause. In particular, it relates to compounds and compositions, particularly topical formulations, comprising the peptides for ameliorating alopecia and other hair diseases.

BACKGROUND ART

Many are the causes of hair loss, and several hair loss types are known, such as alopecia areata, androgenic alopecia, female-pattern alopecia, etc. In addition hair loss can be metabolic syndrome related, due to medication (chemotherapy), a vitamin or mineral deficiency, or due to scalp fungal infections Minoxidil (6-Piperidin-1-ylpyrimidine-2,4-diamine 3-oxide) is one of the active principles mostly used and known in the treatment of alopecia, in particular of androgenic alopecia. Common side effects include burning or irritation of the eye, itching, redness or irritation at the treated area, as well as unwanted hair growth elsewhere on the body. It was disclosed in U.S. Pat. No. 4,139,619 as an ingredient of a topical composition for application to mammalian skin to increase the rate of terminal hair growth. U.S. Pat. No. 4,596,812 discloses the particular use of minoxidil in the treatment of alopecia.

Melatonin was also proposed for the treatment of androgenic female-pattern alopecia in U.S. Pat. No. 6,281,241, in particular due to its effect in reducing the telegenic rate and for occipital hair.

Besides, plant extracts are also proposed with the aim of applying more natural compounds for the treatment of hair loss. As an example, publication of the patent application WO2007113851 proposed novel compositions for hair loss prevention and/or hair growth promotion, in which several extract of *Vernonia* sp. were used as active agents against hair diseases associated in the management of testosterone induced androgenic alopecia.

Other extracts, now of *Curcuma* sp and its active principle curcumin, seemed to avoid hair loss when administered together with resveratrol and other ingredients as deduced from publication of the patent application WO2006087759. Table 1 in Example 1 of WO2006087759 illustrated that some of the treated patients experienced hair growth in bald areas. Also mainly to curcumin present in *Curcuma* sp extracts, the document of Pumthong et al. "*Curcuma aeruginosa*, a novel botanically derived 5α-reductase inhibitor in the treatment of male-pattern baldness: a multicenter, randomized, double-blind, placebo-controlled study", *Journal of Dermatological Treatment.*—2012; vol. no. 23, pp.: 385-392, discloses the use of a *Curcuma aeruginosa* extract (hexane extract) for treating androgenic alopecia. Although meaningful data were achieved with combination of minoxidil and the *Curcuma* extract, the authors postulated that due to its role as 5α-reductase inhibitor, a synergistic effect was observable also due to the direct stimulation of hair growth produced by minoxidil.

Despite all these above-disclosed approaches for treating and/or preventing hair loss, there is still a need of alternative active agents and compositions comprising them for facing hair loss of any cause. In particular there is a need of active agents with proved efficacy, with minimized or null side effects and that can be manufactured in an environmentally and season independent way in case of being derived from plants.

SUMMARY OF THE INVENTION

Inventors surprisingly found that the cell-free supernatants resulting from removal of entire cells in a plant dedifferentiated cell culture suspension contain cocktails of compounds, acting synergistically together with other extracellular products comprised in the supernatant for the purpose of promoting hair growth and the proliferation of hair follicle dermal papilla cells (HFDPC). Moreover, they proved that peptides comprised in isolated peptide fractions of said cell-free supernatants, said peptides mainly involved in plant defence, growth and development were also effective as hair growth promoters and as hair follicle dermal papilla cells proliferation and hair matrix keratinocytes proliferation. Therefore, being both the peptides as well as any fraction of a cell-free supernatant containing them useful in the treatment of hair loss.

In a first aspect, the invention relates to peptide sequences of formula (I), or pharmaceutically, nutraceutical or veterinary acceptable salts thereof, $$(R^1)_{(m)}\text{-Xaa}_1\text{IXaa}_2\text{T(Q)}_{(p)}(R^2)_{(n)} \qquad \text{(I) (SEQ ID NO: 1)}$$

wherein:

$R^1$ is a —C(O)—$(C_1$-$C_{20})$-alkyl radical, acylating N-terminal residue of the peptide sequence;

$R^2$ is a —$NR_4R_5$ radical, amidating C-terminal residue of the peptide sequence, being $R_4$ and $R_5$ selected from H, and $(C_1$-$C_3)$-alkyl;

m, n and p, are integers from 0 to 1; and $Xaa_1$ and $Xaa_2$ are tyrosine residues with the side-chain hydroxyl group optionally replaced by a radical —$OSO_3R^3$; being $R^3$ selected from H and $(C_1$-$C_3)$-alkyl;

for use in the prevention and/or treatment of mammal hair loss in a hair loss causing disease and/or disorder.

This aspect could be also formulated as the use of a peptide sequence of formula (I) or a pharmaceutically, nutraceutical or veterinary acceptable salt thereof, for the preparation of a medicament for the prophylaxis and/or treatment of a mammal hair loss in a mammal hair loss causing disease and/or disorder. It also relates to a method for the prophylaxis and/or treatment of hair loss in a mammal which comprises administering to mammals in need of such treatment an effective amount of a peptide sequence of formula (I) or a pharmaceutically, nutraceutical or veterinary acceptable salt thereof.

As illustrated in the examples below, the peptides of the invention provided a higher effect than minoxidil in terms of HFDPC proliferation. Besides, compositions comprising them, such as cell-free supernatants of plants that previously supported the growth of a dedifferentiated plant cell suspension culture showed also equal or even higher effects than minoxidil.

The peptides proposed for the use according to the invention are compounds miming the phytosulfokine-β (PSK-β), isolated from conditioned media of plant cells in suspension (see Matsubayashi et al., "Phytosulfokine, sulphated peptides that induce the proliferation of single mesophyll cells of Asparagus officinalis L.", *Proc. Natl. Acad. Sci.*—1996, vol. no. 93, pp.: 7623-7627). To the best of inventor's knowledge, this is the first time phytosulfokine-β (PSK-β) or a derivative of phytosulfokine-β (PSK-β) is proposed as a medicament, in particular as hair loss preventing or treating agent.

A second aspect of the invention is a pharmaceutical, nutraceutical or veterinary composition comprising peptides of formula (I), or a pharmaceutically, nutraceutical or veterinary acceptable salt thereof, together with pharmaceutically, nutraceutical or veterinary acceptable excipients and/ or carriers for use in the treatment hair loss in a hair loss causing disease and/or disorder.

Inventors have also developed particular effective compositions, in particular topical compositions to be administered on scalp or the desired bald area. These compositions comprise all those ingredients allowing proliferation of HFDPC and provide to these proliferated cells the materials to allow hair growth. Hair growth is thus effected in scalp, but also in any place where the compositions are applied and where hair is usually present, such as in the lashes, the eyebrows and the beard.

Thus, in a third aspect, the invention relates to pharmaceutical, nutraceutical or veterinary compositions comprising vitamins, amino acids, pharmaceutically, nutraceutical or veterinary acceptable salts of iron, magnesium, copper and zinc, together with pharmaceutically, nutraceutical or veterinary acceptable excipients and/or carriers, the composition further comprising a peptide of formula (I), or a pharmaceutically, nutraceutical or veterinary acceptable salt thereof, and/or a cell-free supernatant of a dedifferentiated plant cell culture suspension, or a fraction of said cell-free supernatant, wherein said cell-free supernatant or said fraction comprises peptides from 4 to 300 amino acids length, said peptides selected from peptide plant growth factors, plant transcription factors, epigenetic factors, and mixtures thereof, said peptide plant growth factors comprising the peptide of formula (I), and said cell-free supernatant or said fraction without having cytoplasmic cell contents from the cell lysis and membranes and/or cell walls.

Another aspect of the invention is a kit comprising:

(a) a peptide sequence of formula (I), or a pharmaceutically, nutraceutical or veterinary acceptable salt thereof; and (b) a pharmaceutical, nutraceutical or veterinary composition comprising vitamins, amino acids, and/or pharmaceutically, nutraceutical or veterinary acceptable salts thereof; pharmaceutically, nutraceutical or veterinary acceptable organic or inorganic salts of iron, magnesium, copper and zinc-, together with pharmaceutically, nutraceutical or veterinary acceptable excipients and/or carriers.

DETAILED DESCRIPTION OF THE INVENTION

Figure 1:
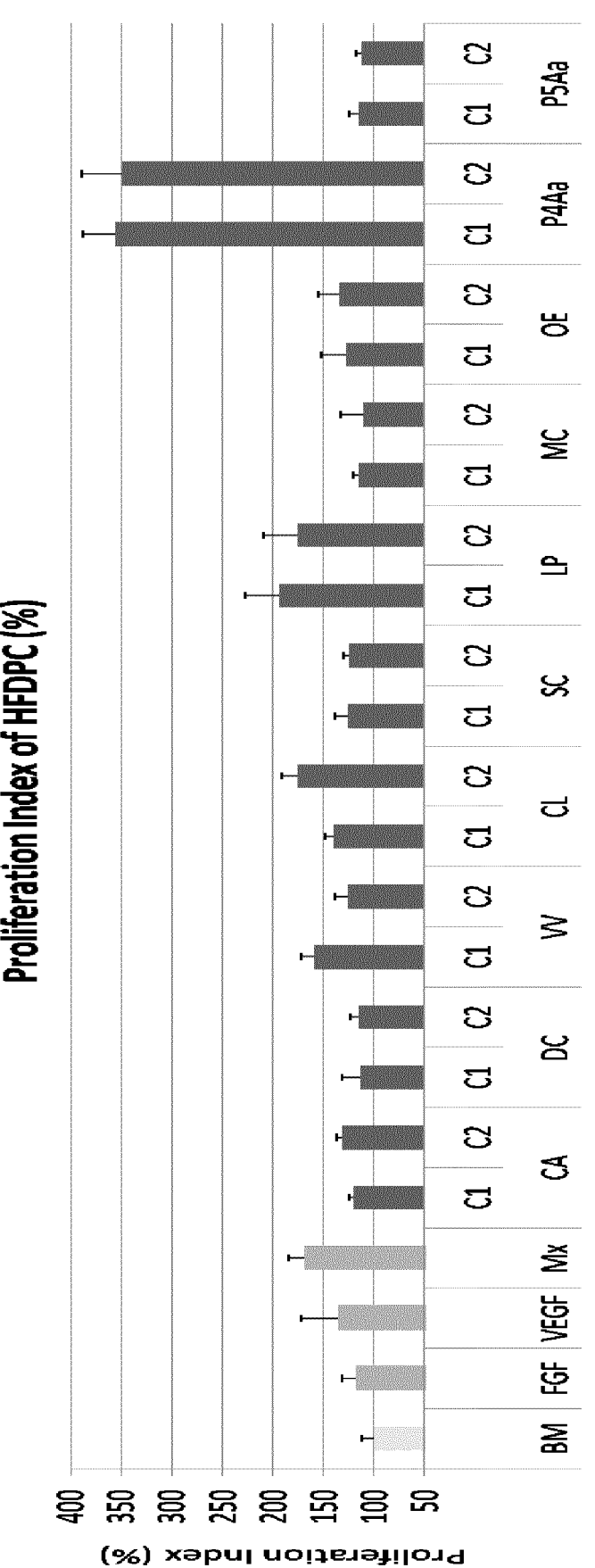
FIG. 1, related with Assay 1, is graph with the proliferation index (%) of hair follicle dermal papilla cells (HFDPC), when treated with several compositions. Ctrl BM means basal control (non-treated HFDPC), which is accorded a 100% value of proliferation index: FGF means fibroblast growing factor, VEGF means vascular endothelial growing factor, C1 and C2 correspond to different concentrations of cell-free supernatants of the tested species, as indicated in Table 1, said supernatants (also known as conditioned media) comprising peptides from 4 to 300 amino acids length. Plant species names have been abbreviated also as indicated in Table 1. Peptide 4Aa and 5Aa are peptides of SEQ ID NO: 6 and 7, respectively. In Y-axis the proliferation index in percentage (%).

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For "mammal hair loss in a hair loss causing disease" it is to be understood that hair is lost or changed in a frequency more than that associated with health or standard hair renewal, or that hair is weakened, or it does not grown again after having fallen, being said "hair loss" caused by any disorder or disease, which symptom or consequence is that the number of hair in a particular area is decreased or the number of hair in a particular area is a weak hair. The "hair loss" may also be due to any other circumstances, such as the medication side effects. In particular the causes, diseases or disorders causing hair loss are to be understood as encompassing: alopecia (i.e. androgenic alopecia, androgenic female-pattern alopecia, alopecia areata, seasonal alopecia, diffuse alopecia, metabolic syndrome related), medication (i.e. chemotherapy), hypotrichosis, vitamin or mineral deficiency, trichotillomania, hypothyroidism, tightly pulled hair, scalp fungal infections, hair loss due to technical processes (due to stressing hair treatments, such as staining), hair fragility and menopause, and combinations thereof.

As used herein, the term "pharmaceutically, nutraceutical or veterinary acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzene-sulfonate, benzoate, bisulfate, borate, butyrate, camphorate, camphorsulfonate, citrate, cyclopentanepropionate, diglu-conate, dodecylsulfate, ethanesulfonate, formate, fumarate, glucoheptonate, glycerophosphate, gluconate, hemisulfate, heptanoate, hexanoate, hydroiodide, 2-hydroxy-ethane-sulfonate, lactobionate, lactate, laurate, lauryl sulfate, malate, maleate, malonate, methanesulfonate, 2-naphthale-nesulfonate, nicotinate, nitrate, oleate, oxalate, palmitate, pamoate, pectinate, persulfate, 3-phenylpropionate, phos-phate, picrate, pivalate, propionate, stearate, succinate, sul-fate, tartrate, thiocyanate, p-toluenesulfonate, undecanoate, valerate salts, and the like. Salts derived from appropriate bases include alkali metal, alkaline earth metal, and ammo-nium. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

"Nutraceutical compositions" are edible compositions including dietary supplements, oral rehydration solutions (ORS), food additives, baby cereals and infant formulas. Dietary supplements intend to supply nutrients, (vitamins, minerals, fatty acids or amino acids) that are missing or not consumed in sufficient quantity in a person's diet (infants, pregnant women, elderly people, etc).

The term "pharmaceutically, nutraceutical or veterinary effective amount" as used herein, means an amount of an active agent high enough to deliver the desired benefit, but low enough to avoid serious side effects within the scope of medical or veterinary judgment.

The term $(C_1$-$C_3)$alkyl refers to a saturated straight or branched alkyl chain having from 1 to 3 carbon atoms. Illustrative non-limitative examples are: methyl, ethyl, pro-pyl, and isopropyl.

The term $-C(O)-(C_1$-$C_{20})$-alkyl radical, refers to a saturated straight or branched alkanoyl acid chain having from 2 to 21 carbon atoms. Illustrative non-limitative examples are: acetyl, propanoyl, isopropanoyl, butanoyl, isobutanoyl, sec-butanoyl, tert-butanoyl, n-pentanoyl, neo-pentanoyl, n-hexanoyl, n-myristoyl (or n-tetradecanoil) and n-palmitoyl (or n-hexadecanoyl). Particular $-C(O)-(C_1$-$C_{20})$-alkyl radicals in the present invention are acetyl, n-myristoyl (or n-tetradecanoil) and n-palmitoyl (or n-hexa-decanoyl).

The term "amino acid" constituting the peptide sequences refers to a molecule containing both an amino group and a carboxyl group. In certain embodiments, an amino acid is an alpha amino acid. Suitable amino acids include, without limitation, natural alpha-amino acids such as L-isomers of the 20 common naturally occurring alpha-amino acids. Amino acids used in the construction of peptides of the present invention may be prepared by organic synthesis, or obtained by other routes, such as, for example, degradation of or isolation from a natural source.

When in the present invention it is indicated that the tyrosine residues are ones in which their side-chain hydroxyl group has been replaced by a radical $-OSO_3R^3$; being $R^3$ selected from H and $(C_1$-$C_3)$-alkyl, it is to be understood as encompassing those sulphated tyrosines ($-OSO3H$) and pharmaceutically acceptable salts thereof (due to ionic equi-librium with counter-ions). Tyrosine sulphation is a naturally occurring posttranslational modification where a sulphate group is added to a tyrosine residue of a protein molecule. Sulphation is catalyzed by tyrosylprotein sulfotransferase (TPST) in the Golgi apparatus. The reaction catalyzed by TPST is a transfer of sulphate from the universal sulphate donor 3'-phosphoadenosine-5'-phosphosulfate (PAPS) to the side-chain hydroxyl group of a tyrosine residue. In synthetic peptides with sulphated tyrosines, enzymatic reactions may be employed, as well as chemical sulphation reactions widely known by the skilled man.

The expression "cell-free supernatant that previously sup-ported the growth of a dedifferentiated plant cell suspension culture" refers only to the liquid that contained the dedif-ferentiated plant cells during growing or cultivation in suspension in a culture medium and for any purpose (pro-duction of secondary metabolites, biomass production, etc.). The cell-free supernatant does not contain the cytoplasm contents released from the lysis of the plant cells, as well as any part of the plant cell resulting from disruption of the same (membrane fragments, cell-wall fragments, etc.). The cell-free supernatant comprises among the ingredients of the initial culture medium that have been not consumed, also those compounds secreted by the plant cells to the extracel-lular media. Among these compounds there are the peptide plant growth factors, transcription factors and epigenetic factors. The cell-free supernatant is also called conditioned nutrient media or conditioned media, or conditioned cell-medium (used herewith interchangeably). When it is said that the cell-free supernatants are "without having cytoplas-mic cell contents from the cell lysis and without having membranes and/or cell walls" is to be understood that traces of some membranes and/or cell walls, and cytoplasmic components (nucleic components, organelles, etc.) can be present due to the spontaneous disruption of isolated cells occurring occasionally during the culturing process.

In a particular embodiment, optionally in combination with any embodiments below, the peptides of formula (I) for use in the prevention and/or treatment of hair loss in a mammal hair-loss causing disease are those, wherein $R^1$ is a $-C(O)-(C_1$-$C_{20})$-alkyl radical selected from $-C(O)-CH_3$ radical, n-myristoyl, and n-palmitoyl.

In another particular embodiment, optionally in combi-nation with any embodiments above or below, the peptides of formula (I) for use in the prevention and/or treatment of hair loss in a mammal hair-loss causing disease are those, wherein $R^3$ of $-OSO_3R^3$ is hydrogen (H), encompassing also salts of alkaline metals of the acid form.

In a further particular embodiment the peptides of formula (I) for use in the prevention and/or treatment of hair loss in a mammal hair-loss causing disease are those wherein m and n are 1 and p is from 0 to 1. More in particular m and n are 1 and p is from 0 to 1, and $R^1$ is a $-C(O)-CH_3$ radical, $R^2$ is a $-NH_2$ radical, and $R_3$ is hydrogen (H).

Examples of these peptides are $CH_3-C(O)-Xaa_1IYT$-$NH_2$ (SEQ ID NO: 2), wherein $Xaa_1$ is a tyrosine residue with the side-chain hydroxyl group replaced by a radical $-OSO_3H$;

$CH_3-C(O)-YIXaa_2T$-$NH_2$ (SEQ ID NO: 3), wherein $Xaa_2$ is a tyrosine residue with the side-chain hydroxyl group replaced by a radical $-OSO_3H$;

$CH_3-C(O)-Xaa_1IYTQ$-$NH_2$ (SEQ ID NO: 4) wherein $Xaa_1$ is a tyrosine residue with the side-chain hydroxyl group replaced by a radical $-OSO_3H$;

$CH_3-C(O)-YIXaa_2TQ$-$NH_2$ (SEQ ID NO: 5), wherein $Xaa_2$ is a tyrosine residue with the side-chain hydroxyl group replaced by a radical $-OSO_3H$;

CH$_3$—C(O)—YIYT-NH$_2$ (SEQ ID NO: 6); and
CH$_3$—C(O)—YIYTQ-NH$_2$ (SEQ ID NO: 7);

In a further particular embodiment the peptides of formula (I) for use in the prevention and/or treatment of hair loss in a mammal hair-loss causing disease are those wherein m is 1, n is 0, and p is from 0 to 1. More in particular wherein m is 1, n is 0, and p is from 0 to 1 and R$^1$ is a —C(O)—CH$_3$ radical, and R$^3$ is H. Examples of these peptides of formula (I) are CH$_3$—C(O)—YIYT (SEQ ID NO: 16); and CH$_3$—C(O)—YIYTQ (SEQ ID NO: 17).

In a further particular embodiment the peptides of formula (I) for use in the prevention and/or treatment of hair loss in a mammal hair-loss causing disease are those wherein m is 0, n is 1, and p is from 0 to 1. More in particular, wherein m is 0, n is 1, and p is from 0 to 1, R$^2$ is a —NH$_2$ radical, and R$^3$ is H. Examples of these peptides of formula (I) are YIYT-NH$_2$ (SEQ ID NO: 18); and YIYTQ-NH$_2$ (SEQ ID NO: 19).

Also in a further particular embodiment the peptides of formula (I) for use in the prevention and/or treatment of hair loss in a mammal hair-loss causing disease are those wherein m and n are both 0, and p is from 0 to 1. Examples of these peptides of formula (I) are Xaa$_1$IYT (SEQ ID NO: 8), wherein Xaa$_1$ is a tyrosine residue with the side-chain hydroxyl group replaced by a radical—OSO$_3$H; YIXaa$_2$T (SEQ ID NO: 9), wherein Xaa$_2$ is a tyrosine residue with the side-chain hydroxyl group replaced by a radical —OSO$_3$H; Xaa$_1$IYTQ (SEQ ID NO: 10) wherein Xaa$_1$ is a tyrosine residue with the side-chain hydroxyl group replaced by a radical —OSO3H; YIXaa$_2$TQ (SEQ ID NO: 11), wherein Xaa$_2$ is a tyrosine residue with the side-chain hydroxyl group replaced by a radical —OSO$_3$H; YIYT (SEQ ID NO: 12); YIYTQ (SEQ ID NO: 13); Xaa$_1$IXaa$_2$T (SEQ ID NO: 14), wherein Xaa$_1$ and Xaa$_2$ are both a tyrosine residue with the side-chain hydroxyl group replaced by a radical —OSO$_3$H; and Xaa$_1$IXaa$_2$TQ (SEQ ID NO: 15), wherein Xaa$_1$ and Xaa$_2$ are both a tyrosine residue with the side-chain hydroxyl group replaced by a radical —OSO$_3$H In other certain embodiments, optionally in combination with any embodiment above or below, the peptides for use according to the invention are selected from the group consisting of:

CH$_3$—C(O)—Xaa$_1$IYT-NH$_2$ (SEQ ID NO: 2), wherein Xaa$_1$ is a tyrosine residue with the side-chain hydroxyl group replaced by a radical —OSO$_3$H;

CH$_3$—C(O)—YIXaa$_2$T-NH$_2$ (SEQ ID NO: 3), wherein Xaa$_2$ is a tyrosine residue with the side-chain hydroxyl group replaced by a radical —OSO$_3$H;

CH$_3$—C(O)—Xaa$_1$IYTQ-NH$_2$ (SEQ ID NO: 4) wherein Xaa$_1$ is a tyrosine residue with the side-chain hydroxyl group replaced by a radical —OSO$_3$H;

CH$_3$—C(O)—YIXaa$_2$TQ-NH2 (SEQ ID NO: 5), wherein Xaa$_2$ is a tyrosine residue with the side-chain hydroxyl group replaced by a radical —OSO$_3$H;

CH$_3$—C(O)—YIYT-NH$_2$ (SEQ ID NO: 6);

CH$_3$—C(O)—YIYTQ-NH$_2$ (SEQ ID NO: 7);

Xaa$_1$IYT (SEQ ID NO: 8), wherein Xaa$_1$ is a tyrosine residue with the side-chain hydroxyl group replaced by a radical —OSO$_3$H;

YIXaa$_2$T (SEQ ID NO: 9), wherein Xaa$_2$ is a tyrosine residue with the side-chain hydroxyl group replaced by a radical —OSO$_3$H;

Xaa$_1$IYTQ (SEQ ID NO: 10) wherein Xaa$_1$ is a tyrosine residue with the side-chain hydroxyl group replaced by a radical —OSO$_3$H;

YIXaa$_2$TQ (SEQ ID NO: 11), wherein Xaa$_2$ is a tyrosine residue with the side-chain hydroxyl group replaced by a radical —OSO$_3$H;

(SEQ ID NO: 12)
YIYT;

(SEQ ID NO: 13)
YIYTQ;

Xaa$_1$IXaa$_2$T (SEQ ID NO: 14), wherein Xaa$_1$ and Xaa$_2$ are both a tyrosine residue with the side-chain hydroxyl group replaced by a radical —OSO$_3$H;

Xaa$_1$IXaa$_2$TQ (SEQ ID NO: 15), wherein Xaa$_1$ and Xaa$_2$ are both a tyrosine residue with the side-chain hydroxyl group replaced by a radical —OSO$_3$H;

(SEQ ID NO: 16)
CH$_3$—C(O)-YIYT;

(SEQ ID NO: 17)
CH$_3$—C(O)-YIYTQ;

(SEQ ID NO: 18)
YIYT-NH$_2$;

(SEQ ID NO: 19)
YIYTQ-NH$_2$;

and mixtures thereof.

In a more particular embodiment, the peptides are selected from the group consisting of:

(SEQ ID NO: 6)
CH$_3$—C(O)-YIYT-NH$_2$;

(SEQ ID NO: 7)
CH$_3$—C(O)-YIYTQ-NH$_2$;

Xaa$_1$IYT (SEQ ID NO: 8), wherein Xaa$_1$ is a tyrosine residue with the side-chain hydroxyl group replaced by a radical —OSO$_3$H;

YIXaa$_2$T (SEQ ID NO: 9), wherein Xaa$_2$ is a tyrosine residue with the side-chain hydroxyl group replaced by a radical —OSO$_3$H;

(SEQ ID NO: 12)
YIYT;

(SEQ ID NO: 13)
YIYTQ;

Xaa$_1$IXaa$_2$T (SEQ ID NO: 14), wherein Xaa$_1$ and Xaa$_2$ are both a tyrosine residue with the side-chain hydroxyl group replaced by a radical —OSO$_3$H;

Xaa$_1$IXaa$_2$TQ (SEQ ID NO: 15), wherein Xaa$_1$ and Xaa$_2$ are both a tyrosine residue with the side-chain hydroxyl group replaced by a radical —OSO$_3$H;

and mixtures thereof.

All these peptides of formula (I) can be formulated in pharmaceutical, nutraceutical or veterinary compositions, wherein they are one of the actives against hair loss. The invention relates, as above exposed, also to those pharmaceutical, nutraceutical or veterinary compositions comprising peptides of formula (I), or a pharmaceutically, nutraceutical or veterinary acceptable salt thereof, together with pharmaceutically or veterinary acceptable excipients and/or carriers for use in the prevention and/or treatment of a hair loss in a hair loss causing disease.

When formulated in pharmaceutical, nutraceutical or veterinary compositions, the peptides of formula (I) may be, in a particular embodiment, conveniently protected against proteases, and/or prepared for penetrating the cells. Agents that facilitate the delivery of the peptide of the invention across a cell membrane without negatively affecting the ability of the peptide to promote cell proliferation and hair growth include penetrating peptides fused or bound thereto; liposomes; and nanoparticles (1-300 nm).

In a particular embodiment of this second aspect, the compositions for the purposed use are topical compositions that are applied onto scalp and/or to bald regions. Particular topical compositions are selected from the group consisting of solutions, creams, lotions, unguents, emulsions, aerosols and non-aerosol sprays, gels, ointments and suspensions, all of them rinse-off and not rinsed compositions. Hair growth is thus effected in any place where the compositions are applied and where hair is usually present, such as in the lashes, the eyebrows, the scalp and the beard.

In another particular embodiment of the second aspect the pharmaceutical, nutraceutical or veterinary compositions for the purposed use further comprise vitamins, amino acids, pharmaceutically or veterinary acceptable organic or inorganic salts of iron, magnesium, copper and zinc.

Indeed, these compositions further comprising the vitamins, metal salts and amino acids, provide to the treated area or to the area where they are applied the mixture of cell nutrients (as a reinforcing composition) that allow papilla cells and papilla matrix (keratinocytes) forming or producing new hair.

In a more particular embodiment the pharmaceutical, nutraceutical or veterinary compositions for the purposed use comprise the vitamins selected from the group consisting of vitamin C, vitamin B1, vitamin B3, vitamin B5, vitamin B6, vitamin B2, biotin (which is the water soluble vit B8), vitamin B9, myo-inositol, and mixtures thereof.

In another also more particular embodiment, the pharmaceutical, nutraceutical or veterinary compositions for the purposed use comprise amino acids, or salts thereof, selected from the group consisting of glutamic acid, phenylalanine, glycine, methionine, proline, cysteine and mixtures thereof. In another particular embodiment protein hydrolysates, more in particular casein hydrolysates, are comprised therein.

In another particular embodiment, the pharmaceutical, nutraceutical or veterinary composition for use as above indicated, is that in which the weight ratio of iron to copper is from 25:1 to 900:1, of zinc to copper is from 30:1 to 400:1, and of magnesium to copper is from 570:1 to 5800:1. Weight ratio between elements relates to the weight of the element in the formulation. In another more particular embodiment, in combination with the embodiments above or below, the weight ratio of iron to copper is from 700:1 to 900:1, of zinc to copper is from 300:1 to 400:1, and of magnesium to copper is from 2300:1 to 5800:1. Particular weight ratios of all the elements as Fe/Cu/Zn/Mg are: 868/1/307/5730; and 25/1/307/2856.

Yet in another also more particular embodiment, the pharmaceutical, nutraceutical or veterinary compositions for the purposed use comprise as the acceptable salts of iron, magnesium, copper and zinc the inorganic salts selected from the group consisting of iron sulphate, copper sulphate, zinc sulphate, magnesium sulphate, and mixtures thereof.

In another particular embodiment, the pharmaceutical, nutraceutical or veterinary composition for use as above indicated, comprises a peptide of formula (I), or a pharmaceutically or veterinary acceptable salt thereof, vitamin C, vitamin B1, vitamin B2, vitamin B3, vitamin B5, vitamin B6, vitamin B8, vitamin B9, glycine, methionine, phenylalanine, proline, cysteine, glutamic acid, zinc sulphate, copper sulphate, magnesium sulphate and iron sulphate together with pharmaceutically, nutraceutical or veterinary acceptable excipients and/or carriers.

In a particular embodiment of the pharmaceutical, nutraceutical or veterinary composition for use as above disclosed, and also optionally in combination with any embodiments above or below, the peptide of formula (I) is provided in the composition as an ingredient comprised in, or of a cell-free supernatant that previously supported the growth of a dedifferentiated plant cell suspension culture, or a fraction of said cell-free supernatant, wherein said cell-free supernatant or said fraction comprises peptides from 4 to 300 amino acids length, said peptides selected from peptide plant growth factors, plant transcription factors, epigenetic factors and mixtures thereof, and said cell-free supernatant or said fraction without having cytoplasmic cell contents from the cell lysis and membranes and/or cell walls.

Many of these cell-free supernatants or fractions thereof are commercially available.

They can also be generically obtained by a method comprising:
- (a) growing dedifferentiated plant cells from a friable callus in a liquid nutrient culture medium from 5 to 15 days, to obtain a conditioned media supporting the growth of the dedifferentiated plant cells;
- (b) removing entire plant cells from the conditioned media without lysing the cells, to obtain a cell-free supernatant comprising peptides from 4 to 300 amino acids length; and
- (c) optionally carrying out a protein separation process by means of a separation technique selected from the group consisting of chromatography, filtration, ultrafiltration, protein precipitation, and combinations thereof, to obtain a fraction of the cell-free supernatant.

In another particular embodiment, the pharmaceutical, nutraceutical or veterinary composition for use as above proposed, comprises the peptide of formula (I) provided in the composition as an ingredient of a cell-free supernatant of a dedifferentiated plant cell culture suspension from a plant selected from the group consisting of *Daucus carota, Centella asiatica, Sarcocapnos crassifolia, Curcuma longa, Vitis vinifera, Lithops pseudotruncatella, Morinda citrifolia*, and *Olea europaea*.

Indeed, these cell-free supernatants or fractions thereof comprising peptides from 4 to 300 amino acids length may be the natural source of the peptides of formula (I), which in the examples are demonstrated as highly active.

In another particular embodiment of the first and second aspects, the peptide sequence of formula (I) or a pharmaceutically, nutraceutical or veterinary acceptable salt thereof, or the pharmaceutical, nutraceutical or veterinary composition comprising it, are for use in the prevention and/or treatment of mammal hair loss (in particular human hair loss) in a mammal hair loss causing disease or disorder selected from alopecia, medication (in particular chemotherapy), hypotrichosis, vitamin or mineral deficiency, trichotillomania, hypothyroidism, tightly pulled hair, scalp fungal infections, hair loss due to technical processes, hair fragility, menopause, and combinations thereof.

In another particular embodiment, the peptide sequence of formula (I) or a pharmaceutically, nutraceutical or veterinary acceptable salt thereof, or the pharmaceutical, nutraceutical or veterinary composition comprising it, are for use in the prevention and/or treatment of mammal hair loss of scalp, beard, lashes and eyebrows. This means that they are for use also for promoting hair growth in beard, for elongating lashes and for increasing density of hair in the eyebrow area.

In particular, the peptides of formula (I), salts thereof, or any composition comprising them are for use in the prevention and/or treatment of alopecia selected from androgenic alopecia, androgenic female-pattern alopecia, alopecia areata, seasonal alopecia, diffuse alopecia, metabolic syndrome related alopecia.

According to the third aspect, the invention relates to pharmaceutical, nutraceutical or veterinary compositions comprising vitamins, amino acids, pharmaceutically, nutraceutical or veterinary acceptable organic or inorganic salts of iron, magnesium, copper and zinc, together with pharmaceutically, nutraceutical or veterinary acceptable excipients and/or carriers, the compositions further comprising:

a peptide of formula (I), or a pharmaceutically, nutraceutical or veterinary acceptable salt thereof, and/or
  a cell-free supernatant of a dedifferentiated plant cell culture suspension, or a fraction of said cell-free supernatant, wherein said cell-free supernatant or said fraction comprises peptides from 4 to 300 amino acids length, said peptides selected from peptide plant growth factors, plant transcription factors, epigenetic factors, and mixtures thereof, said peptide plant growth factors comprising the peptide of formula (I), and said cell-free supernatant or said fraction without having cytoplasmic cell contents from the cell lysis and membranes and/or cell walls.

The invention relates, in particular, also to new topical pharmaceutical or veterinary compositions comprising vitamins, amino acids, pharmaceutically acceptable organic or inorganic salts of iron, magnesium, copper and zinc, together with pharmaceutically or veterinary acceptable excipients and/or carriers, the composition further comprising:

a peptide of formula (I), or a pharmaceutically or veterinary acceptable salt thereof, and/or
  a cell-free supernatant of a dedifferentiated plant cell culture suspension, or a fraction of said cell-free supernatant, wherein said cell-free supernatant or said fraction comprises peptides from 4 to 300 amino acids length, said peptides selected from peptide plant growth factors, plant transcription factors, plant epigenetic factors and mixtures thereof, said peptide plant growth factors comprising the peptide of formula (I), and said cell-free supernatant or said fraction without having cytoplasmic cell contents from the cell lysis and membranes and/or cell walls.

In a particular embodiment of these pharmaceutical, nutraceutical or veterinary compositions, and so also of the topical pharmaceutical or veterinary compositions, the cell-free supernatant of a dedifferentiated plant cell culture suspension, or a fraction of said cell-free supernatant are from a plant selected from the group consisting of *Daucus carota, Centella asiatica, Sarcocapnos crassifolia, Curcuma longa, Vitis vinifera, Lithops pseudotruncatella, Morinda citrifolia*, and *Olea europaea*.

In another particular embodiment of the pharmaceutical, nutraceutical or veterinary compositions, and so also of the topical pharmaceutical or veterinary compositions according to the invention, the peptide of formula (I) is particularly selected from:

$CH_3$—C(O)—YIYT-$NH_2$ (SEQ ID NO: 6);
  $CH_3$—C(O)—YIYTQ-$NH_2$ (SEQ ID NO: 7);

$Xaa_1$IYT (SEQ ID NO: 8), wherein $Xaa_1$ is a tyrosine residue with the side-chain hydroxyl group replaced by a radical —$OSO_3H$;
  YIX$aa_2$T (SEQ ID NO: 9), wherein $Xaa_2$ is a tyrosine residue with the side-chain hydroxyl group replaced by a radical —$OSO_3H$;
  YIYT (SEQ ID NO: 12);
  YIYTQ (SEQ ID NO: 13);
  $Xaa_1$IX$aa_2$T (SEQ ID NO: 14), wherein $Xaa_1$ and $Xaa_2$ are both a tyrosine residue with the side-chain hydroxyl group replaced by a radical —$OSO_3H$;
  $Xaa_1$IX$aa_2$TQ (SEQ ID NO: 15), wherein $Xaa_1$ and $Xaa_2$ are both a tyrosine residue with the side-chain hydroxyl group replaced by a radical —$OSO_3H$;
  $CH_3$—C(O)—YIYT (SEQ ID NO: 16);
  $CH_3$—C(O)—YIYTQ (SEQ ID NO: 17);
  YIYT-$NH_2$ (SEQ ID NO: 18);
  YIYTQ-$NH_2$ (SEQ ID NO: 19);
  and mixtures thereof.

In a more particular embodiment of the pharmaceutical, nutraceutical or veterinary compositions, and so also of the topical pharmaceutical or veterinary compositions according to the invention, it comprises a peptide of formula (I), or a pharmaceutically, nutraceutical or veterinary acceptable salt thereof; vitamins, amino acids, and pharmaceutically, nutraceutical or veterinary acceptable salts of iron, magnesium, copper and zinc, wherein the weight ratio of iron to copper is from 25:1 to 900:1, of zinc to copper is from 30:1 to 400:1, and of magnesium to copper is from 570:1 to 5800:1.

In also another particular embodiment of this aspect of the invention, the pharmaceutical, nutraceutical or veterinary composition comprises a peptide of formula (I), or a pharmaceutically or veterinary acceptable salt thereof; vitamin C, vitamin B1, vitamin B2, vitamin B3, vitamin B5, vitamin B6, vitamin B8, vitamin B9, glycine, methionine, phenylalanine, proline, cysteine, glutamic acid, zinc sulphate, copper sulphate, magnesium sulphate and iron sulphate together with pharmaceutically, nutraceutical or veterinary acceptable excipients and/or carriers. In yet a more particular embodiment, the peptide of formula (I) is selected from $CH_3$—C(O)—YIYT-$NH_2$ (SEQ ID NO: 6); $CH_3$—C(O)—YIYTQ-$NH_2$ (SEQ ID NO: 7);

$Xaa_1$IYT (SEQ ID NO: 8), wherein $Xaa_1$ is a tyrosine residue with the side-chain hydroxyl group replaced by a radical —$OSO_3H$;
  YIX$aa_2$T (SEQ ID NO: 9), wherein $Xaa_2$ is a tyrosine residue with the side-chain hydroxyl group replaced by a radical —$OSO_3H$;
  YIYT (SEQ ID NO: 12);
  YIYTQ (SEQ ID NO: 13);
  $Xaa_1$IX$aa_2$T (SEQ ID NO: 14), wherein $Xaa_1$ and $Xaa_2$ are both a tyrosine residue with the side-chain hydroxyl group replaced by a radical —$OSO_3H$;
  $Xaa_1$IX$aa_2$TQ (SEQ ID NO: 15), wherein $Xaa_1$ and $Xaa_2$ are both a tyrosine residue with the side-chain hydroxyl group replaced by a radical —$OSO_3H$;
  $CH_3$—C(O)—YIYT (SEQ ID NO: 16);
  $CH_3$—C(O)—YIYTQ (SEQ ID NO: 17);
  YIYT-$NH_2$ (SEQ ID NO: 18);
  YIYTQ-$NH_2$ (SEQ ID NO: 19);
  and mixtures thereof. More in particular is SEQ ID NO: 6

The combination of the peptides of formula (I) and the compositions (solutions) comprising salts of iron, copper, magnesium and zinc, together with vitamins and amino acids of the invention, has a synergistic effect in terms of proliferation of human dermal fibroblasts (HDF). This makes the combination useful in the treatment of hair loss but also as tissue regeneration agent.

As indicated, one aspect of the invention is a kit comprising:

(a) a peptide sequence of formula (I), or a pharmaceutically, nutraceutical or veterinary acceptable salt thereof; and (b) a pharmaceutical, nutraceutical or veterinary composition comprising vitamins, amino acids, and/or pharmaceutically, nutraceutical or veterinary acceptable salts thereof; pharmaceutically, nutraceutical or veterinary acceptable organic or inorganic salts of iron, magnesium, copper and zinc-, together with pharmaceutically, nutraceutical or veterinary acceptable excipients and/or carriers.

This kit allows preparing in situ the synergistic combination of the invention.

The invention also relates to pharmaceutical, nutraceutical or veterinary compositions comprising vitamins, amino acids, or pharmaceutically, nutraceutical or veterinary acceptable salts thereof; pharmaceutically, nutraceutical or veterinary acceptable organic or inorganic salts of iron, magnesium, copper and zinc; together with pharmaceutically, nutraceutical or veterinary acceptable excipients and/or carriers; wherein the weight ratio of iron to copper is from 25:1 to 900:1, of zinc to copper is from 30:1 to 400:1, and of magnesium to copper is from 570:1 to 5800:1.

In a particular embodiment of these compositions, the weight ratio of iron to copper is from 700:1 to 900:1, of zinc to copper is from 300:1 to 400:1, and of magnesium to copper is from 2300:1 to 5800:1.

As will be depicted in the assays below, these compositions are by themselves highly effective in terms of allowing proliferation of human hair follicle papilla cells (HFDPC), human dermal fibroblasts (HDF) and human immortalized keratinocytes (HaCat). This feature makes the compositions good for use as a medicament for skin treatment, in particular for alleviating senescence processes of skin, and/or for skin wound healing. In addition, they are for use in the prevention and/or treatment of mammal hair loss (in particular human hair loss) in a mammal hair loss causing disease or disorder. They are also good regenerating and reparation skin agents. Thus they can be used as ingredients of cosmetic compositions.

Particular weight ratios of all iron, cooper, zinc and magnesium from the salts are, indicated as Fe/Cu/Zn/Mg: 868/1/307/2326-5730; and 868/1/307/5730.

In a particular embodiment, the pharmaceutical, nutraceutical or veterinary compositions of the invention, comprise vitamin C, vitamin B1, vitamin B2, vitamin B3, vitamin B5, vitamin B6, vitamin B8, vitamin B9, glycine, methionine, phenylalanine, proline, cysteine, glutamic acid, zinc sulphate, copper sulphate, magnesium sulphate and iron sulphate together with pharmaceutically, nutraceutical or veterinary acceptable excipients and/or carriers.

In another particular embodiment, the pharmaceutical, nutraceutical or veterinary compositions comprise protein hydrolysate, thiamine, niacin, pantothenic acid, pyridoxine, biotin, folic acid, riboflavin, ascorbic acid, citric acid, myo-inositol, calcium chloride, magnesium sulphate, potassium dihydrogenphosphate, zinc sulphate, copper sulphate, and iron ethylendiaminetetraacetic chelate. More in particular, it comprises casein hydrolysate.

These compositions, as well as the peptides of formula (I), are proliferation-inducing agents of mammal fibroblasts and of mammal dermal papilla cells. Therefore, the invention lies in these are proliferation-inducing agents, selected from peptides of formula (I), and pharmaceutical, nutraceutical or veterinary compositions as defined above, or mixtures thereof, for use in the prevention and/or treatment of a hair loss in a hair loss causing disease.

The invention also relates to cell-free supernatants that previously supported the growth of a dedifferentiated plant cell suspension culture, or a fraction of said cell-free supernatant, for use in the prevention and/or treatment of mammal hair loss in a mammal hair-loss causing disease, wherein said cell-free supernatant or said fraction comprises peptides from 4 to 300 amino acids length, said peptides selected from peptide plant growth factors, plant transcription factors, plant epigenetic factors and mixtures thereof, and said cell-free supernatant or said fraction without having cytoplasmic cell contents from the cell lysis and membranes and/or cell walls.

These supernatants without the inner content of cell cytoplasm and without the cell membranes and/or walls are herewith termed conditioned nutrient media or conditioned media, or conditioned cell-medium. The cell-free supernatants of the invention contain thus, not only amounts of those compounds initially present in the culture media where dedifferentiated plant cells were grown and that were not consumed, but also other compounds that dedifferentiated plant cells released to the media. It is thus proposed the use of these conditioned media without the dedifferentiated cells, or of a fraction thereof comprising these peptide plant growth factors and/or transcription factors and/or epigenetic factors for prevention and/or treatment of mammal hair loss in a mammal hair loss causing disease, and more particularly hair loss in humans.

The fractions of said cell-free supernatants comprising peptides from 4 to 300 amino acids length, being plant growth factors, plant epigenetic factors or plant transcription factors, can also be defined as "isolated" compositions (or isolated fractions) comprising peptides from 4 to 300 amino acids length and obtainable from the cell-free supernatant that previously supported the growth of a dedifferentiated plant cell suspension culture. In particular, isolation of such compositions comprise separating or recovering a liquid from the said supernatant with the peptide plant growth factors by means of at least a protein separation process, said process comprising at least one of chromatography (selected from solid-phase extraction (SPE), size-exclusion chromatography (SEC), and combination in cascade thereof), filtering (in particular by tangential flow filtration (TFF)), protein precipitation, and combinations thereof. These compositions comprising peptide plant growth factors and/or plant transcription factors so obtained are, in particular, for use as skin animal cells repairing and/or regenerating agents, and for use in the prevention and/or treatment of mammal hair loss in a mammal hair-loss causing disease, as above exposed.

In a particular embodiment, the cell-free supernatant of a dedifferentiated plant cell culture suspension, or a fraction thereof that comprises peptides from 4 to 300 amino acids length for use in the prevention and/or treatment of mammal hair loss in a mammal hair-loss causing disease, is selected from a plant of the group consisting of *Daucus carota, Curcuma longa, Centella asiatica, Sarcocapnos crassifolia, Vitis vinifera, Lithops pseudotruncatella, Morinda citrifolia,* and *Olea europaea.*

More in particular the cell-free supernatant of a dedifferentiated plant cell culture suspension, or a fraction thereof that comprises peptides from 4 to 300 amino acids length, for use in the prevention and/or treatment of mammal hair loss in a mammal hair-loss causing disease is of *Curcuma longa*.

In a another particular embodiment, these cell-free supernatants or isolated fractions thereof include peptide cocktails, said cocktails comprising at least a peptide plant growth factors selected from the group consisting of Phytosulphokine-α (PSK-α), Phytosulphokine-β (PSK-β), Plant Peptide Containing Sulphated Tyrosine-1 (PSY1), Rapid Alkalinization Factor (RALF), Tracheary Element Differentiation Inhibitory Factor (TDIF), Clavata-3 (CLV3), Clavata-Embryo Surrounding Region-Related (CLE), Tapetum Determinant-1 (TPD1), Epidermal Patterning Factor-1 (EPF1), Inflorescence Deficient in Abscission (IDA), Embryo Surrounding Region-Related (ESR), Polaris peptide (PLS), Root meristem Growth Factor (RGF), Egg Cell-Secreted Protein (EC1), C-terminally Encoded peptide (CEP), Early Nodulin 40 (ENOD40), Systemin, S-locus Cystein Rich proteins (SCR), and mixtures thereof, which means a combination of all of them, of only two, three, four or more than two until comprising all of the listed peptides.

The cell-free supernatants or isolated fractions thereof include the peptides of formula (I) of particular SEQ ID NO: 14 and 15. Thus, they are also source of the active in hair loss treatment peptides of the invention.

Other peptides than peptide plant growth factors are also present in a particular embodiment of the cell-free supernatants that previously supported the growth of a dedifferentiated plant cell suspension culture, or a fraction of said cell-free supernatants. These peptides are in particular peptide plant transcription factors, including among others Wound-Induced Dedifferentiation (WIND), Wuschel (WUS), Teosinte Branched1/Cycloidea/Proliferating Cell Factor (TCP), and transcriptional factor for root meristem maintenance (PLETHORA), and mixtures thereof. These transcription factors regulate shoot meristem formation, stem cell maintenance and somatic cell differentiation.

Traces of other compounds, usually known as epigenetic factors, are also comprised in the cell-free supernatants, or a fraction of said cell-free supernatants due to the residual disruption of some cells during culturing (as above enunciated), which can deliver the nuclear and cytoplasm contents in the culture media, although reduced to minimal amounts. Examples of these plant epigenetic factors are selected from the group consisting of Chromomethylase (CMT), Domains Rearranged Methyltransferase (DRM), Methyltransferase (MET), and some auxins, involved in the NA methylation processes; the chromatin remodelling factor PICKLE of the CHP family (the CHD proteins derive their name from the presence of three domains of sequence similarity: a Chromatin organization modifier domain (chromodomain), a SWI2/SNF2 ATPase/Helicase domain, and a motif with sequence similarity to a DNA-binding domain), the chromatin remodelling factor DDM1 (from Decrease In DNA Methylation-1), involved in decondensation and remodelling of chromatin; the histone H3 methyltransferase Kryptonite (KYP), involved in remodelling of histones; small RNA molecules; and mixtures of all these proteins and compounds. Epigenetic factors are to be understood as those biomolecules, particularly of peptide nature, that control marks in a cell for the DNA controlling expression or silencing of genes.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1.—Preparation of Peptides of Formula (I)

Assayed peptide sequences were assembled by solid phase methods using a Fmoc-based protection scheme on a Rink amide resin. The side chain of the Tyr (Y) residues was protected with a t-butyl group. Deprotection of the N-terminal Fluorenylmethyloxycarbonyl chloride (Fmoc) groups was done with 20% piperidine in dimethylformamide (DMF) in 5 min. Synthesis was performed in a Prelude automated synthesizer (Protein Technologies, Tucson, AZ, USA). After chain assembly, the peptide-resin was treated with 90% trifluoroacetic acid-5% triisopropylsilane-5% water for 1 h, the corresponding filtrate was treated with 3 volumes of chilled ethyl ether to precipitate the peptide. After centrifugation, the supernatant was carefully removed and he pellet (containing the peptides) were redissolved in aqueous (5% v/v) acetic acid and lyophylized. Purification of the crude product was done by preparative reverse-phase HPLC using water/acetonitrile gradients (both with 0.05% trifluoroacetic acid). The purified peptides were homogeneous (>95%) by HPLC and had the expected molecular mass by electrospray mass spectrometry.

With this methodology the following sequences were obtained and assayed as will be illustrated in the next assays: $CH_3$—C(O)—YIYT-$NH_2$ (SEQ ID NO: 6), $CH_3$—C(O)—YIYTQ-$NH_2$ (SEQ ID NO: 7), YIYT (SEQ ID NO: 12), YIYTQ (SEQ ID NO: 13), $CH_3$—C(O)—YIYT (SEQ ID NO: 16), $CH_3$—C(O)—YIYTQ (SEQ ID NO: 17), YIYT-$NH_2$ (SEQ ID NO:18). and YIYTQ-$NH_2$ (SEQ ID NO: 19).

For in vivo assays (see below) acetyl tetrapeptide (SEQ ID NO: 6) was dissolved (0.025% w/w) in a buffered solution containing salts, vitamins and aminoacids. This buffered solution was as follows:

500 ml/L of a fortifying solution at 2x
Prepared from (a) a 100x solution, 30 ml/L [wherein the 100x fortifying solution comprised $ZnSO4·5H2O$ (860 mg/L); 100 μl $CuSO4·5H2O$ solution (25 g of $CuSO4·5H2O$ per liter of Fe solution), $MgSO4·5H2O$ (18054 mg/L), Vitamine C (5000 mg/L), Vitamin B1 (thiamine, 50 mg/L), vitamin B3 (niacin, 50 mg/L), vitamin B5 (D-panthothenate calcium, 50 mg/L), vitamin B6 (pyridoxine, 50 mg/L), glycine (2000 mg/L), methionine (3000 mg/L), phenylalanine (1500 mg/L), proline (3000 mg/L), cysteine (3000 mg/L), glutamic acid (750 mg/L), q.s. of $FeSO4·7H2O$ solution ($Na2EDTA·2H2O$ (4.46 g/L), $FeSO4·7H2O$ (3.503 g/L) in miliQ water];
(b) vitamin stock solution 5x, 400 ml/L [wherein the vitamin stick solution 5x is vitamin B2 (riboflavin, 2.5 mg/L), biotin 2.5 mg/L, vitamin B9 (folic acid, 2.5 mg/L) in miliQ water;
(c) an amino acid stock solution 20x, 100 ml/L [wherein the 20x is glutamic acid (450 mg/L), L-phenilalanine (300 mg/L) in miliQ water]

(d) Preservative 1%, 10 ml/L (e) in 1 L of miliQ water.

500 ml/L of phosphate buffered saline (PBS) 2× at pH 6.8

For in vitro assays on hair follicle dermal papilla cells (HFDPC), human dermal fibroblasts (HDF), or immortalized epidermal keratinocytes (HaCat), synthesized peptides (SEQ ID NO: 6, SEQ ID NO: 7, SEQ ID NO: 12, SEQ ID NO: 13, SEQ ID NO: 16, SEQ ID NO: 17, SEQ ID NO: 18, and SEQ ID NO: 19.) were dissolved in the culture media. The HFDPC were from normal human hair follicles from temporal scalp from a single donor: 54 years old caucasian male were used (Ref. 602-05a. Lot. 2092. of CELL APPLICATIONS, INC). The HDF were obtained from were obtained from foreskin samples, surpluses from surgery of young donors (0-3 years old) and stablished by using the standard method of explants growth and enzymic dissociation of proliferating cells. And the immnortalized human keratinocytes (HaCat) were obtained from aneuploid immortal keratinocyte cell line from adult human skin

Example 2.—Preparation of Cellfree Supernatants of *Curcuma longa* and of Formulations Comprising Them for In Vivo Assays

*C. longa* Conditioned Media

It consisted of the extracellular media of a *Curcuma longa* cell suspension mixed with water and/or glycerol (1:1).

The process for obtaining cell-free *Curcuma longa* cell suspension was carried out by:

Equal volumes (1:1) of the extracellular media of a *Curcuma longa* cell culture at 1° brix were mixed with a fortifying solution containing minerals (inorganic salts), vitamins and amino acids. Brix degrees measures the amount of dry solids dissolved in a sample. This solids can be sugar, salts, etc. and is a mode of determining cell growth in cultures. Both components (extracellular media of a *Curcuma longa* and fortifying solution) were prepared separately and then mixed as:

*Curcuma longa* cells were cultured in SunB media as a cell suspension until the supernatant was 1° brix.

The suspension was filtered using a 0.80 μm monofilament polyesther filter.

1% Geogard Ultra was added as a preservative to the extracellular media recovered by filtration.

Magnetic stirring was needed to properly incorporate the preservative.

Equal volume of the fortifying solution (2×, as above) for conditioned media was added to the extracellular media

Assay 1. In Vitro Proliferation of Human Fibroblasts of Hair Follicle Dermal Papilla Cells (HFDPC)

In order to test the effects of the cell-free supernatants, as well as of the peptides of the invention, a proliferation assay was conducted onto human hair follicle papilla cells (CELL APPLICATIONS, INC; Normal human hair follicles from temporal scalp. Single donor: 54 years old caucasian male; Ref. 602-05a. Lot. 2092.).

Next Table 1 shows tested material and controls in FIG. 1:

| Assayed samples in FIG. 1 |
| --- |
| Basal control (Ctrl): non-treated cells maintained in culture media |
| Positive control: cells treated with fibroblast growing factor (FGF) |

-continued

| Assayed samples in FIG. 1 |
| --- |
| Positive control: cells treated with vascular endothelial growing factor (VEGF) |
| Minoxidil (Mx) ((≥99% (TLC)), SIGMA, Ref. M4145. Stock solution: 16.67 mg/ml in Ethanol (25 mg Minoxidil + 1.5 ml Ethanol). |
| *Centella asiatica* (CA) 3.0 μg/ml C1 and 6.0 μg/ml C2 |
| *Curcuma longa* (CL): 3.0 μg/ml C1 and 6.0 μg/ml C2 |
| *Daucus carota* (DC): 1.6 μg/ml C1 and 1.5 μg/ml C2 (at 48 h) |
| *Vitis vinifera* (W): 6.3 μg/ml C1 and 12.5 μg/ml C2 |
| *Sarcocapnos crassifolia* (SC): 12.5 μg/ml C1 and 25.0 μg/ml C2 |
| *Morinda citrifolia* (MC): 3.1 μg/ml C1 and 6.0 μg/ml C2 |
| *Olea europaea* (OE): 25.0 μg/ml C1 and 50.0 μg/ml C2 |
| *Lithops* Sp. (LP): 3.0 μg/ml C1 and 1.5 μg/ml C2 |
| Peptide 4Aa (CH₃—C(O)-YIYT-NH₂) (SEQ ID NO: 6): 5.0 μg/ml C1 and 2.5 μg/ml C2 |
| Peptide 5Aa (CH₃—C(O)-YIYTQ-NH₂) (SEQ ID NO: 7): 0.04 μg/ml C1 and 0.2 μg/ml C2 |

Figure 2:
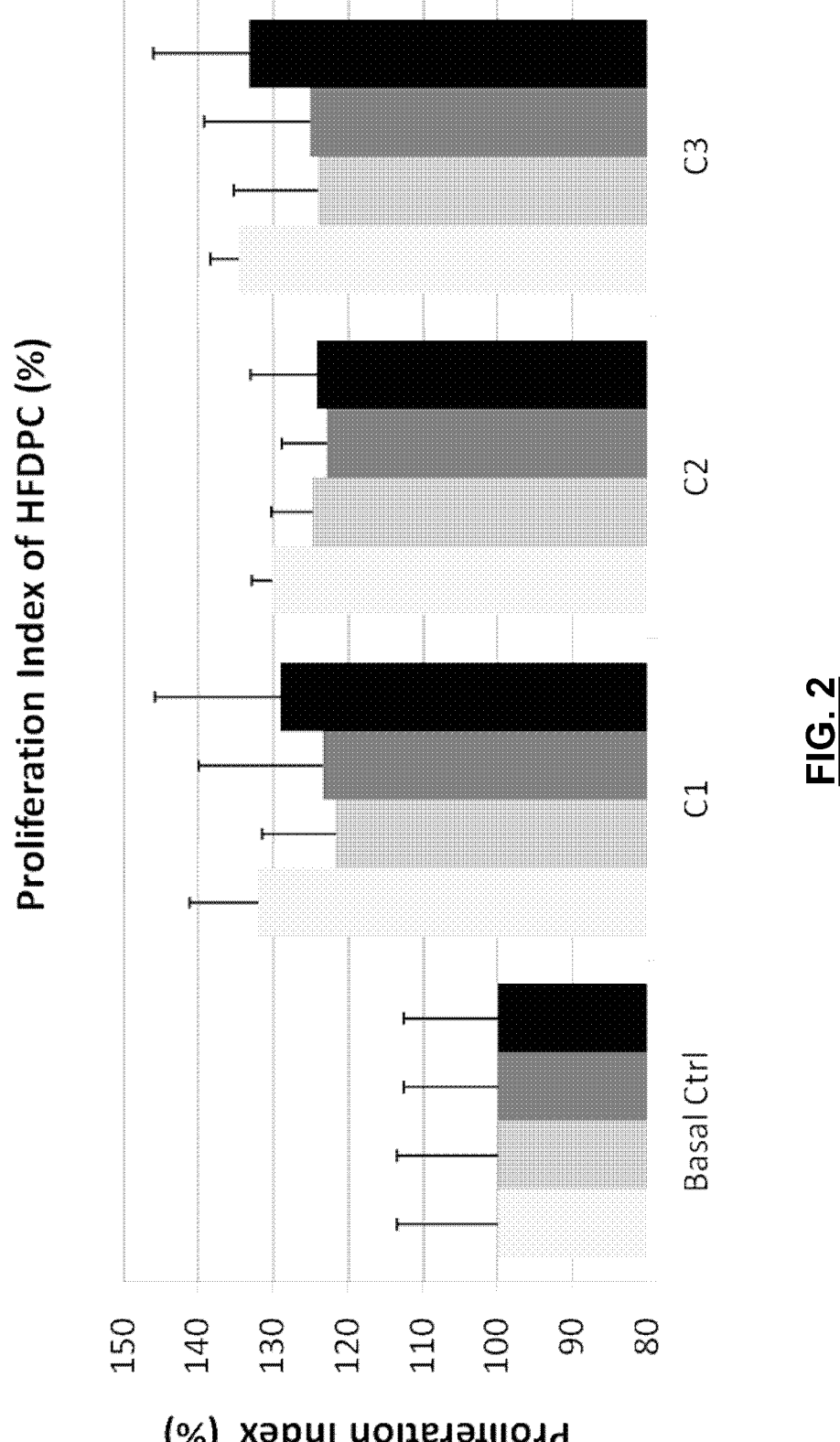
FIG. 2, related with Assay 1, is a graph with the proliferation index (%) of hair follicle dermal papilla cells (HFDPC), when treated with the peptide 4Aa carrying various end-terminal modifications. "Basal Ctrl" means basal control (non-treated HFDPC), which is accorded a 100% value of proliferation index. C1, C2 and C3 represent different concentrations of peptides, corresponding to 5.86 μg/ml, 2.93 μg/ml and 1.46 μg/ml, respectively. The first column corresponds to the 4Aa peptide wherein both ends are free (SEQ ID NO:12); the second column corresponds to the 4Aa peptide wherein the N-terminal end is acetylated the C-terminal end is free (SEQ ID NO:16); the third column corresponds to the 4Aa peptide wherein the N-terminal end is free and the C-terminal end is amidated (SEQ ID NO:18); and the forth column corresponds to the 4Aa peptide wherein the N-terminal end is acetylated and the C-terminal end is amidated (SEQ ID NO: 6).
Figure 3:
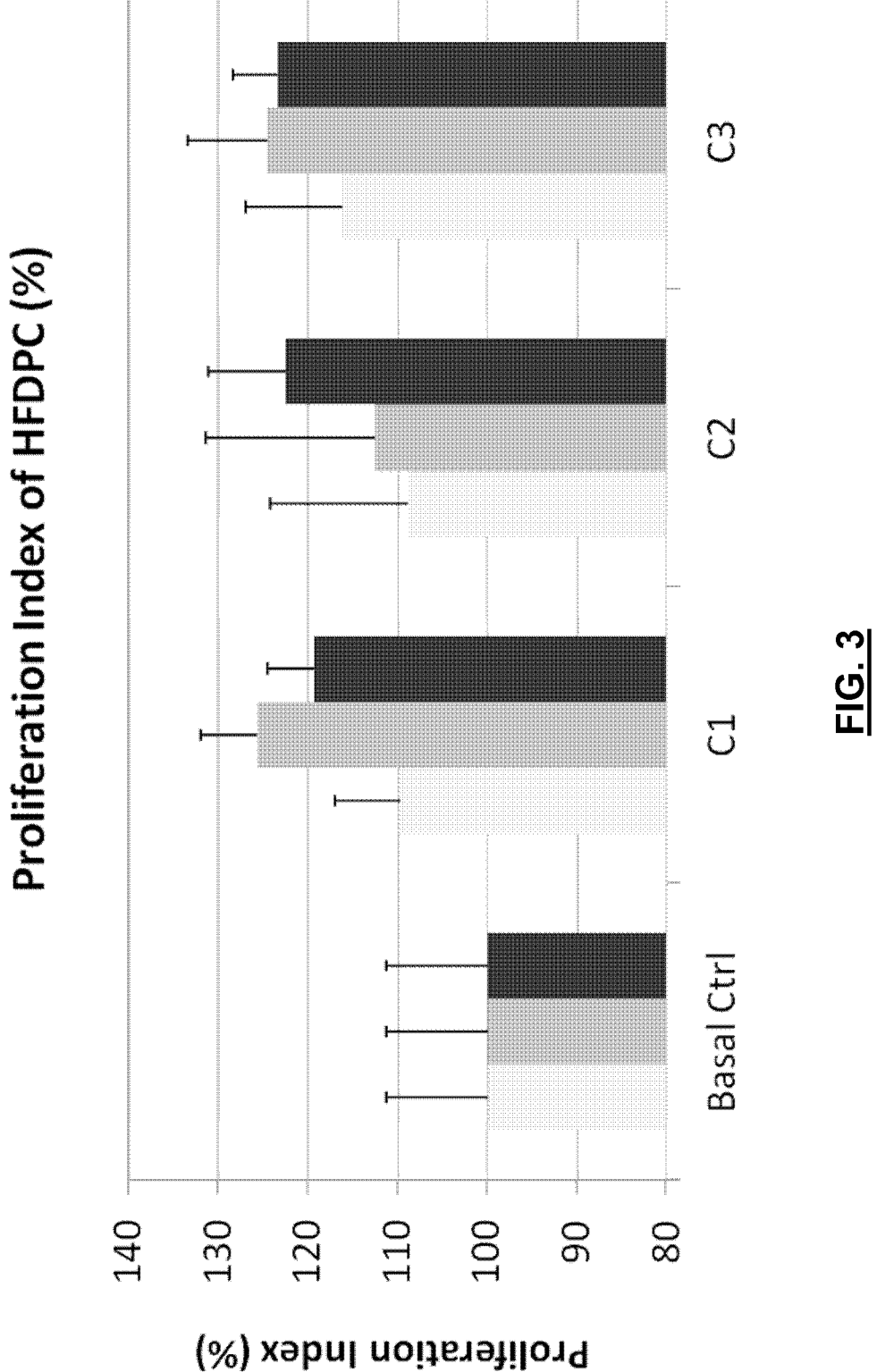
FIG. 3, related with Assay 1, is a graph with the proliferation index (%) of hair follicle dermal papilla cells (HFDPC), when treated with the peptide 5Aa carrying various end-terminal modifications. "Basal Ctrl" means basal control (non-treated HFDPC), which is accorded a 100% value of proliferation index. C1, C2 and C3 represent different concentrations of peptides, corresponding to 5.86 μg/ml, 2.93 μg/ml and 1.46 μg/ml, respectively. The first column corresponds to the 5Aa peptide wherein both ends are free (SEQ ID NO:13); the second column corresponds to the 5Aa peptide wherein the N-terminal end is acetylated the C-terminal end is free (SEQ ID NO:17); the third column corresponds to the 5Aa peptide wherein the N-terminal end is acetylated and the C-terminal end is amidated (SEQ ID NO: 7).

Next Table 2 shows the evaluated concentrations of peptides in FIGS. 2 and 3:

| Peptide | C1 (μg/ml) | C2 (μg/ml) | C3 (μg/ml) |
| --- | --- | --- | --- |
| P4Aa | 5.83 | 2.93 | 1.46 |
| P5Aa | 5.86 | 2.93 | 1.46 |

The culture media was a Papilla Cell Basal Medium supplemented with the Growth Supplements kit (Relative composition: Fetal bovine serum, growth factors and antibiotics. Application: 6% v/v).

The cell-free supernatants (also labelled as Pre-pre-LyoP3) were obtained in particular as follows:

Cell suspension cultures of tested species were obtained from inoculums of cell suspensions grown at 200 ml. The inoculums (⅕ of inoculum in relation to the total volume of culture) were inoculated into 2000-ml flasks containing 800 ml of Murashige & Skoog (MS) liquid medium supplemented with 20-30 g/L of sucrose (for example, 30 g), and hormones and placed in a rotary shaker at 100 rpm in the dark at 25° C. Cell cultures were grown for 12 days, when they were clarified (i.e. the cells were removed avoiding lysis) by centrifugation at 4600 rpm for 30 min, to obtain the conditioned media, which was further studied. In order to better purify the conditioned media, a TFF (Tangencial Flow Filtration) was done in the resulting product. The process comprised; a flux step, an equilibration, a filtration, a diafiltration and a final sanitization step. During the process, 2.5 l of PBS, 2.5 l of 20% Ethanol and NaOh 1N were used. After that TFF, a Reverse phase purification (RP) was done (Oligo purification) with the aim of recovering those compounds secreted by plant cells during growing in suspension. The purification included 9 steps: addition of 5 Column volume (CV) water trifluoroacetic acid (TFA) 0.1%, addition of 5 CV CAN TFA 0.1%, inclusion of 5 CV water TFA 0.1% and the addition of TFA to achieve 0.1%. Then the sample was loaded, collected and washed with a 1 CV water TFA 0.1%. The elution was fractionated in 25-50-5-100% CAN with TFA 0.1%. The product was evaporated and resuspended in RP A. At the end of this purification pre-conditioned media 2 (pre cell-free supernatant) was obtained. This pre-conditioned media 2 was purified using a CEX (Cation exchange chromatography) and a AEX (Emphaze hybrid purifier). The process comprised 16 steps; addition of 5CV CEX A (sodium acetate 50 mM pH 4.5), 5 CV CEX B (Sodium acetate 50 mM NaCl 1M pH 4.5) and 5CV CEX A. A dilution 1:5 and a pH adjust to 4.5 with CEX A was also done such a sample loading, a collection of the sample, a washing with 1 CV CEX A and a fractioned elution with CEX B at 125 mM-250 mM-500 mM-1M. The elution received: 5 CV AEX A (Glycine 50 mM pH 9), 5 CV AEX B (Glycine 50 mM NaCl 1 M at a pH 9) and 5 CV AEX A. A dilution 1:5 in AEX A and an adjust to pH 9 was done, as well as a sample loading, a collection of the sample, a washing with 1 CV AEX A and a fractioned elution with AEX B at 125 mM-250 mM-500 mM-1M. A final cell-free suspension (labeled Pre pre-LyoP 3) was obtained. It was then lyophilized and resuspended for use at the desired concentrations.

Materials

RP A: Water TFA 0.1%
RP B: CAN TFA 0.1%
CEX A: Sodium acetate 50 mM pH 4.5
CEX B: Sodium acetate 50 mM pH 4.5
AEX A: Glycine 50 mM pH 9
AEX B: Glycine 50 mM NaCl 1M pH 9

Assayed peptides were those synthesized as in Example 1.

HFDPC proliferation was assessed determining the proliferation index (%). Cell DNA replication was quantified by means of incorporated bromodeoxiuridine (BrdU) into DNA of treated cells. BrdU assay allows measuring cell proliferation based on cell capability of incorporating BrdU during S-phase of the cell cycle. Cells being divided incorporated BrdU that is further detected by means of antibodies and immunocytochemistry detection.

Cells were seeded at confluence in a 96-well plate. After stabilization and synchronization of cell cultures the tested products were added (at the final concentration indicated in Table 1 of Examples. After that, BrdU was added to cultures and HFDPC were incubated at 37° C. until complete BrdU incorporation. BrdU amounts were proportional to the number of cell divisions and thus to the growth of the treated culture.

Data are depicted in FIG. 1, FIG. 2 and FIG. 3, wherein it is shown the proliferation index (%) of HFDPC, calculated as the percentage of growing in relation to the basal control (non-treated HFDPC) which is accorded a 100% value of proliferation index.

As can be seen in FIG. 1, cell-free supernatants of the invention promoted cell proliferation taking as reference or basal control the non-treated cells cultured with media. For some species, the cell-free supernatants comprising the peptides with a molecular weight equal or lower than 30 kDa (from 4 to 300 amino acids length) the proliferation index was much higher even than positive controls. If not, proliferation index was of the same order than the positive controls. Furthermore tested peptide of SEQ ID NO: 6 showed the best results. Thus, confirming that peptides, as defined in the invention, are useful in the treatment of mammal (in particular human) hair loss.

As can be observed in both FIGS. 2 and 3, the peptides 4Aa and 5Aa can promote cell proliferation independently of whether modifications are present in their end termini (columns 2-4) or not (column 1).

In order to determine the presence of the active peptides in the assayed cell-free supernatants, an HPLC chromatography was performed of the cell-free supernatant of *Daucus Carota, Curcuma longa* and *Centella asiatica* (prepared as indicated in Assay 1) and of a peptide of SEQ ID NO: 6. HPLC was performed as follows:

The powder of lyophilized cell cultures of *Centella asiatica, Daucus carota* and *Curuma longa* were resuspended in 2 mL of Water (0.1% NaOH 1M), vortex and centrifuged at 10000 rcf during 5 min. Then the supernatant was filtered through a 0.45 cellulose filter and injected at the HPLC. The HPLC system consisted in a Waters 1795 chromatograph, a Waters Spherisorb® 5 μM OLDS2 4.6 μM×250 mm column and DAD detector Waters 2996. The mobile phase consisted of Water+TFA 0.045% (A) and Acetonitrile+TFA 0.036% (B) at the following gradient (t (min), % B): (0, 0), (4, 0), (19, 100), (23, 0), (25, 0). The injection volume was 20 μL, the flow rate was 1 mL/min and the wavelength was set at set at 220 nm. Retention time of the peptide was 12.2 min.

Figure 4:
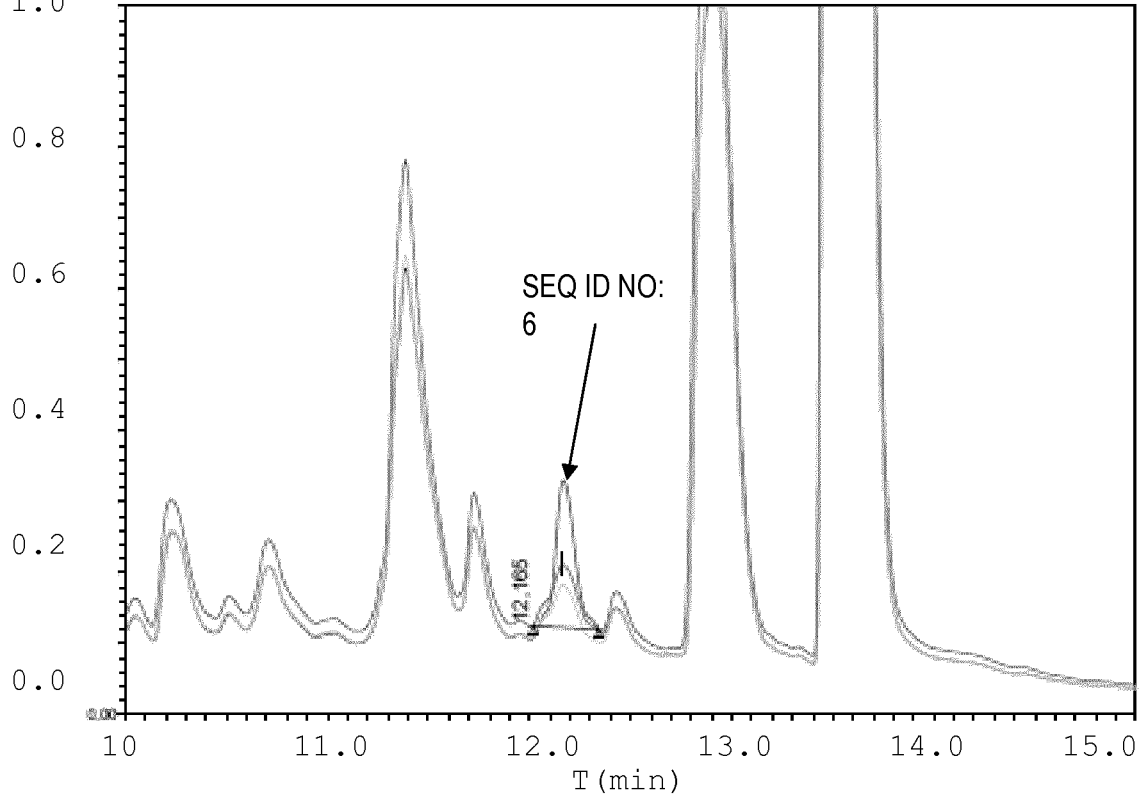
FIG. 4, related with Assay 1, is an HPLC chromatogram of a *Daucus Carota* cell-free supernatant and a peptide of SEQ ID NO: 6. Y-axis, intensity of peaks, X-axis, retention time (T) in minutes (min).

From 12.0 to 12.5 minutes of elution (in particular at 12.165) the *Daucus carota* sample presented a peak as in the peptide chromatogram. These data are depicted in FIG. 4. Due to the natural source of the peptide detected in *Daucus carota*, derived from PSK-beta, the peptide sequence was that of SEQ ID NO: 14.

Although data not shown, SDS PAGE gels of the cell-free supernatants of *Curcuma longa* and *Centella asiatica* showed protein bands at 100 KDa, ≈37 KDa, ≈20 KDa, under 15 KDa and at 2 KDa for *Centella asiatica*. For *Curcuma longa* there were also observed bands at 100 KDa, ≈25 KDa, and under 15 KDa. The bands a under 15 KDa and more in particular in the band at 2 kDa contain the peptides of formula (I) in any of its sulphated or non-sulphate options.

Secretomas (supernatants that could be recovered from the HFDPC cultures challenged with the tested materials of Table 1) were analysed for detecting the presence and levels of animal cell growth factors and of microRNAs associated with hair growth in dermal papilla. Although data not shown, levels of insulin growth factor 1 (IGF-1) determined at 24 h and 48 h after treatment with the compounds of Table 1 were higher than in non-treated HFDPCs and comparable or even higher than minoxidil treated cells. These higher levels were meaningful when HFDPC were treated with the peptide of SEQ ID NO: 6. Similar results (at 24 and 48 h) were observed when analysing the levels of fibroblast growth factor 7 (FGF-7). Both growth factors are associated with the promotion of hair growth.

Figure 5:
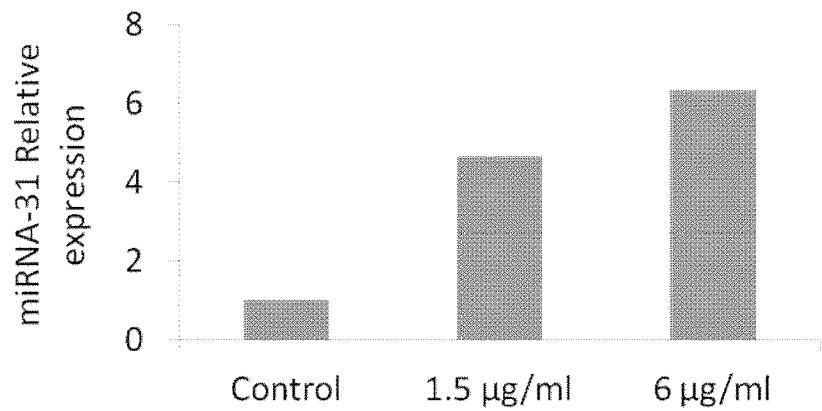
FIG. 5, related with Assay 1, is a graph showing the expression levels of miRNA-22 (FIG. 5(B)) and miRNA-31 (FIGS. 5(A) and (C)) in secretomas from HFDPC treated with either the peptide of SEQ ID NO: 6 or the cell-free supernatants of *Curcuma longa*.
Figure 5:
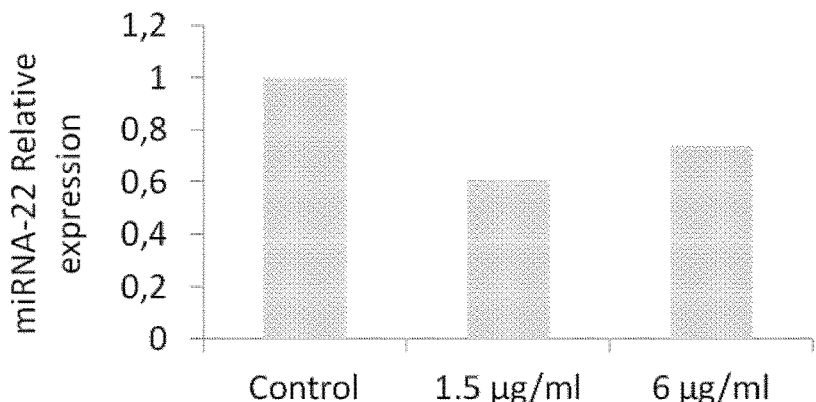
Figure 5:
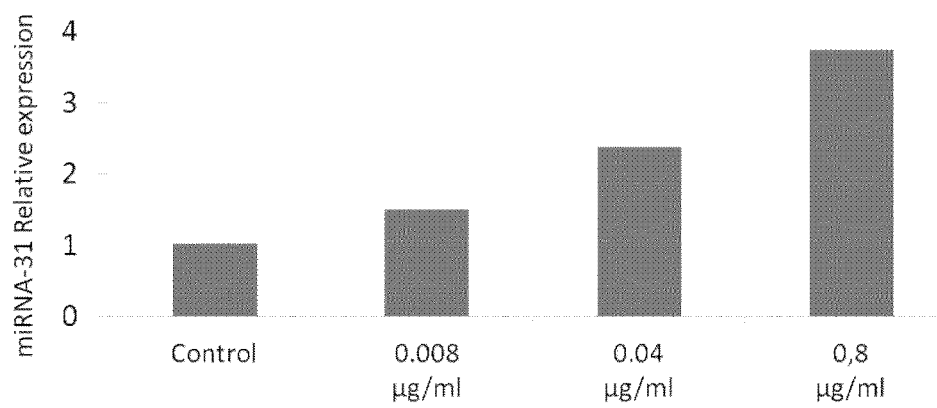

From these secretomes of HFDPC, also the levels of the microRNAs miRNA-31 and miRNA-22 were detected (FIG. 5). The peptide of SEQ ID NO: 6, as well as the cell-free supernatant of *Curcuma longa* (CL) showed an increase of the expression index of miRNA-31 (FIG. 5 (C) for the peptide at three different concentrations and (A) for *Curcuma longa* cell-free supernatant at two different concentrations), in relation to the controls. Besides, the cell-free supernatant of *Curcuma longa* at two different concentrations also showed a decrease of the expression index of miRNA-22 (FIG. 5(B)), in relation to the controls. miRNA-31 is associated with the promotion of hair growth, and miRNA-22 with a the promotion of hair loss (hair fall for the hair renewal).

Assay 2. In Vitro Proliferation of Human Dermal Fibroblasts (HDF)

In order to further test the effects of the peptides of the invention in an additional setting, a proliferation assay was conducted onto human dermal fibroblasts (HDF).
Cell Model:

Normal Human Dermal Fibroblasts (HDF) were obtained from foreskin samples, surpluses from surgery of young donors (0-3 years old) and stablished by using the standard method of explants growth and enzymic dissociation of proliferating cells. Cells were propagated and grown in Growth Medium (GM): Dulbecco's 1 g/L glucose medium, supplemented with 10% foetal bovine serum (FBS, PAA); 2 mM L-glutamine (Lonza); and antibiotics (100 μg/ml Penicillin and 100 U/ml of Streptomycin, Lonza). For routine subcultivation and propagation of the primary culture, cells were washed twice with PBS (Phosphate Phosphate buffered saline, pH 7.4), harvested with trypsin—EDTA (Gibco) and counted in Neubauer chamber before its seeding in a new cell culture flask (Falcon, 75 cm2).

Assayed peptides were those synthesized as in Example 1.

Test products were prepared at the defined final concentrations by its dilution in Maintenance Medium (Dulbecco's 1 g/L glucose medium, supplemented with 1% foetal bovine serum (FBS, PAA); 2 mM L-glutamine (Lonza); and antibiotics (100 μg/ml Penicillin and 100 U/ml of Streptomycin, Lonza), just before each application.

Figure 6:
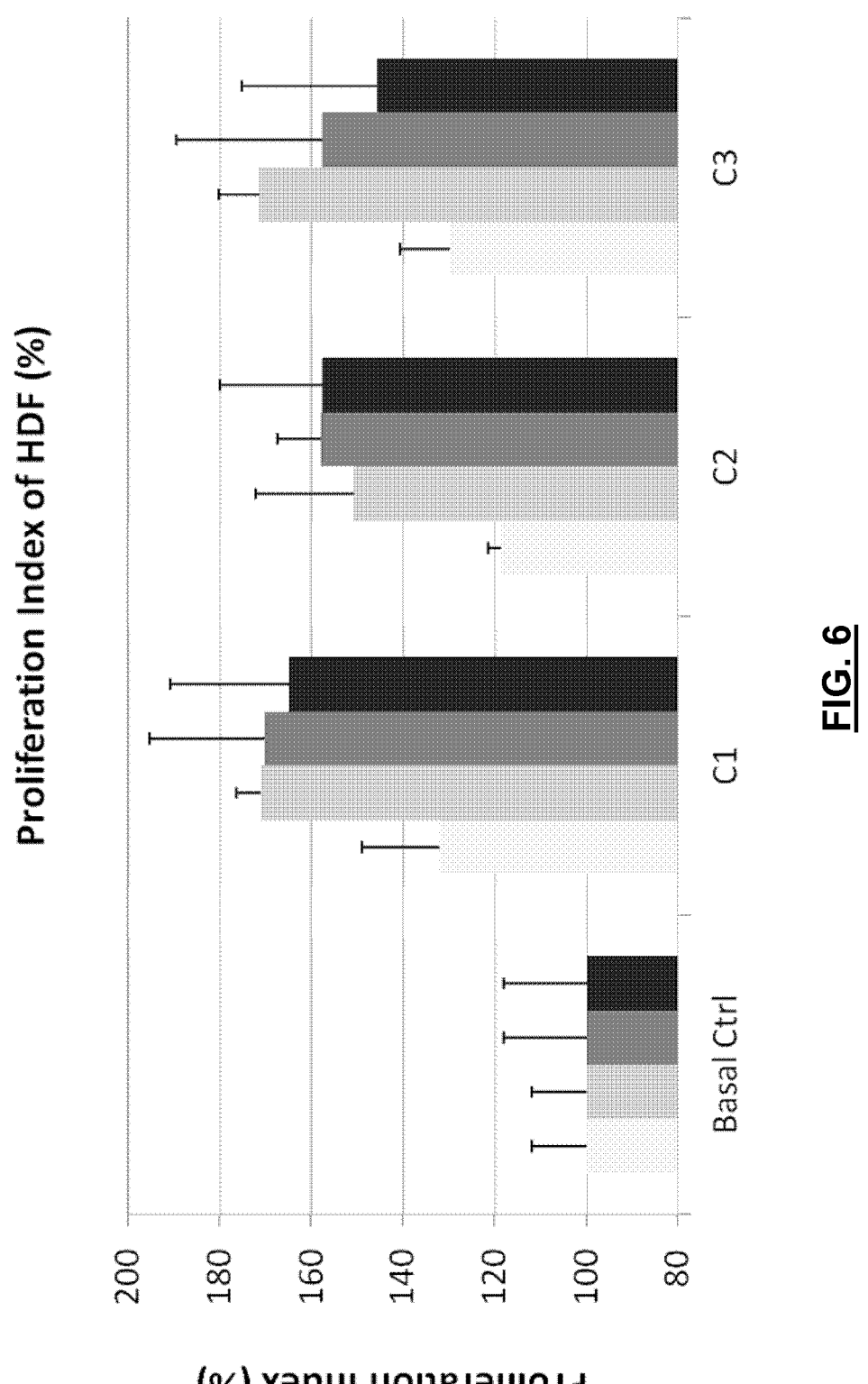
FIG. 6, related with Assay 2, is a graph with the proliferation index (%) of hair dermal fibroblasts (HDF), when treated with the peptide 4Aa carrying various end-terminal modifications. "Basal Ctrl" means basal control (non-treated HDF), which is accorded a 100% value of proliferation index. C1, C2 and C3 represent different concentrations of peptides, corresponding to 25 μg/ml, 12.5 μg/ml and 1.25 μg/ml, respectively. The first column corresponds to the 4Aa peptide wherein both ends are free (SEQ ID NO:12); the second column corresponds to the 4Aa peptide wherein the N-terminal end is acetylated the C-terminal end is free (SEQ ID NO:16); the third column corresponds to the 4Aa peptide wherein the N-terminal end is free and the C-terminal end is amidated (SEQ ID NO:18); and the forth column corresponds to the 4Aa peptide wherein the N-terminal end is acetylated and the C-terminal end is amidated (SEQ ID NO: 6).
Figure 7:
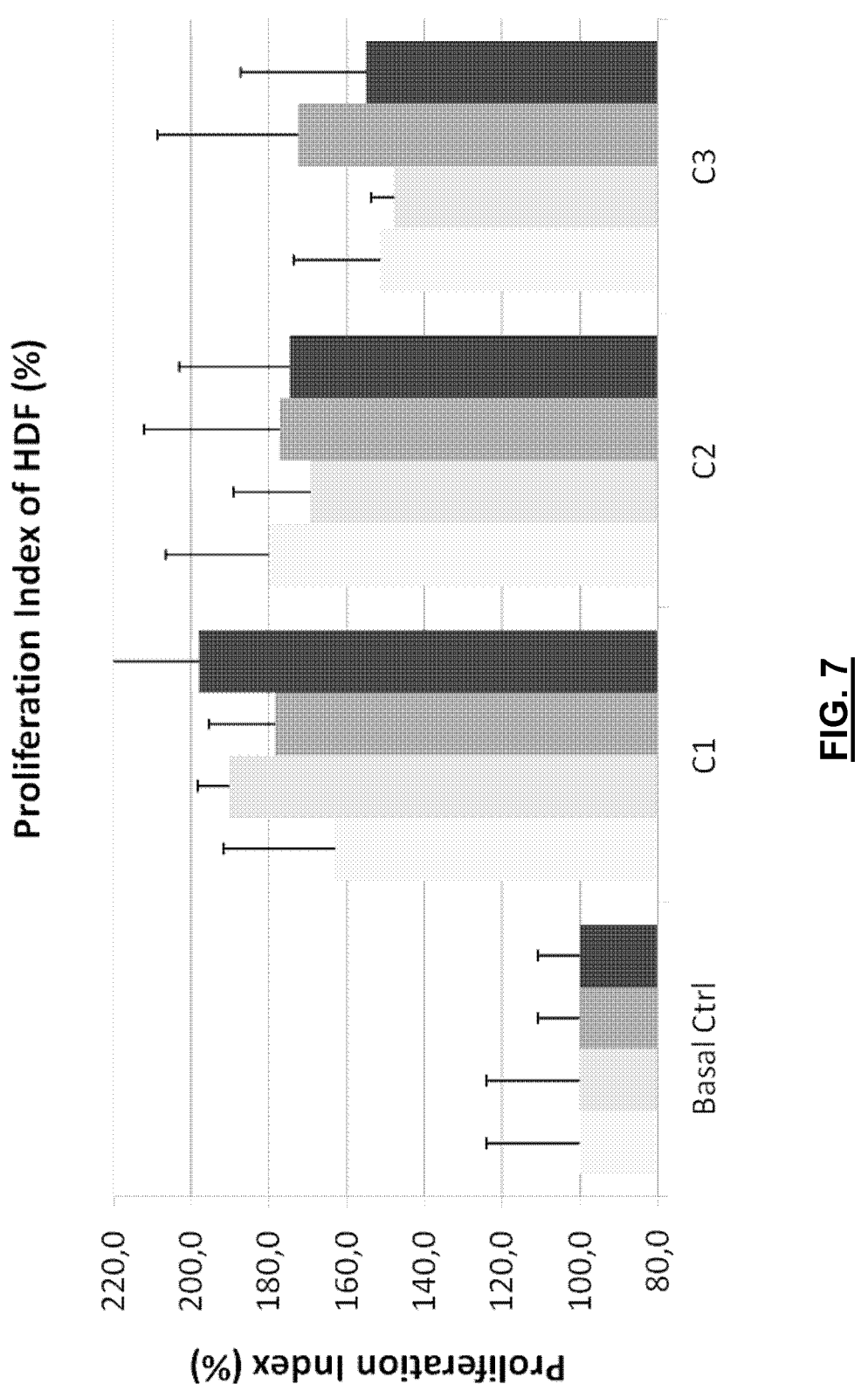
FIG. 7, related with Assay 2, is a graph with the proliferation index (%) of hair dermal fibroblasts (HDF), when treated with the peptide 5Aa carrying various end-terminal modifications. "Basal Ctrl" means basal control (non-treated HDF), which is accorded a 100% value of proliferation index. C1, C2 and C3 represent different concentrations of peptides, corresponding to 1.25 μg/ml, 0.63 μg/ml and 0.25 μg/ml, respectively. The first column corresponds to the 5Aa peptide wherein both ends are free (SEQ ID NO:13); the second column corresponds to the 5Aa peptide wherein the N-terminal end is acetylated the C-terminal end is free (SEQ ID NO:17); the third column corresponds to the 5Aa peptide wherein the N-terminal end is free and the C-terminal end is amidated (SEQ ID NO:19); and the forth column corresponds to the 5Aa peptide wherein the N-terminal end is acetylated and the C-terminal end is amidated (SEQ ID NO: 7).

Next Table 3 shows the evaluated concentrations of FIGS. 6 and 7, for each peptide of formula (I):

| Peptide | C1 (μg/ml) | C2 (μg/ml) | C3 (μg/ml) |
|---------|-----------|-----------|-----------|
| P4Aa | 25 | 12.5 | 1.25 |
| P5Aa | 1.25 | 0.63 | 0.25 |

In FIG. 6, the first column corresponds to the 4Aa peptide wherein both ends are free (SEQ ID NO:12); the second column corresponds to the 4Aa peptide wherein the N-terminal end is acetylated the C-terminal end is free (SEQ ID NO:16); the third column corresponds to the 4Aa peptide wherein the N-terminal end is free and the C-terminal end is amidated (SEQ ID NO:18); and the forth column corresponds to the 4Aa peptide wherein the N-terminal end is acetylated and the C-terminal end is amidated (SEQ ID NO: 6).

In FIG. 7, the first column corresponds to the 5Aa peptide wherein both ends are free (SEQ ID NO:13); the second column corresponds to the 5Aa peptide wherein the N-terminal end is acetylated the C-terminal end is free (SEQ ID NO:17); the third column corresponds to the 5Aa peptide wherein the N-terminal end is free and the C-terminal end is amidated (SEQ ID NO:19); and the forth column corresponds to the 5Aa peptide wherein the N-terminal end is acetylated and the C-terminal end is amidated (SEQ ID NO: 7).

HFD proliferation was assessed determining the proliferation index (%). Cell DNA replication was quantified by means of incorporated bromodeoxiuridine (BrdU) into DNA of treated cells. BrdU assay allows measuring cell proliferation based on cell capability of incorporating BrdU during S-phase of the cell cycle. Cells being divided incorporated BrdU that is further detected by means of antibodies and immunocytochemistry detection.

Cells were seeded at confluence in a 96-well plate. After stabilization and synchronization of cell cultures the tested products were added. After that, BrdU was added to cultures and HFD were incubated at 37° C. until complete BrdU incorporation. BrdU amounts were proportional to the number of cell divisions and thus to the growth of the treated culture.

Data are depicted in FIG. 6 and FIG. 7, wherein it is shown the proliferation index (%) of HDF, calculated as the percentage of growing in relation to the basal control (non-treated HDF) which is accorded a 100% value of proliferation index.

As it was observed in experiments performed on HFDPC, FIGS. 6 and 7 reveal that both 4Aa and 5Aa peptides can promote cell proliferation of HDF independently of whether modifications are present in their end termini (columns 2-4) or not (column 1). In the case of the 4Aa peptide, FIG. 6 shows that the presence of at least one modification further increases it cell proliferation-promoting activity.

Assay 3. In Vivo Test of Peptides of Formula (I) and of Cell-Free Supernatants of *Curcuma longa*

*Curcuma longa* cell-free supernatant prepared as indicated in Example 2, as well as the peptide of SEQ ID NO: 6 in the PBS buffered fortifying solution 2× disclosed in Example 1 were tested in males and females (n=60, from 18 to 60 years old) with hair-loss problems. There were excluded those volunteers that received a capillary treatment three months before the assay, volunteers with cutanic pathologies at scalp (psoriasis, dermatitis, etc.) and allergy to compounds in the formulations.

Tested compounds were daily applied.

At time 0 (T0) there were taken scalp pictures (frontal and occipital parts), trichograms for determining the hair phase cycle (telogen or anagen phase), the combing test (number of hair lost during combing), and capillary density by microphotography with Trichoscan®.

At t=45 days and t=90 days, there were performed the combing test and the density tests (Trichoscan®)

At t=150 days again as in t=0.

Volunteers were separated in three groups. Group 1 receiving SEQ ID NO: 6 in the PBS buffered fortifying solution 2× disclosed in Example 1; Group 2 receiving *Curcuma longa* cell-free supernatant prepared as indicated in Example 2, and Group 3 the placebo.

Data are depicted in next Table 2 for capillary density. This table includes the average values determined of capillary density increase after evaluating in each volunteer the number of hairs in a 0.25 cm$^2$ are, capillary density at t=0 and t=90, and said increase in relation to t=0 value

TABLE 4

| Increase in capillary density | |
|---|---|
| Group | Capillary density increase |
| 1 (volunteers 1 to 20, males and females) | 14.66% |
| 2 (volunteers 21 to 40, males and females) | 15.61% |
| 3 (volunteers 41 to 60, males and females) | 2.80% |

In Table 5, more detailed results of hair density and hair density increase of volunteers of group 1:

TABLE 5

| | Nr HAIRS/ 0.25 cm2 | | | HAIR DENSITY 1/cm2 | | | HAIR DENSITY INCREASE | HAIR DENSITY INCREASE |
|---|---|---|---|---|---|---|---|---|
| Voluntary | T0 | T90 | T150 | T0 | T90 | T150 | T90 | T150 |
| 1 | 31 | 31 | 31 | 123.31 | 123.31 | 123.31 | 0.00% | 0.00% |
| 2 | 15 | 21 | 26 | 59.67 | 83.53 | 103.42 | 39.99% | 73.32%(*) |
| 3 | 31 | 34 | 34 | 123.31 | 135.24 | 135.24 | 9.67% | 9.67% |
| 4 | 26 | 29 | 37 | 103.42 | 115.35 | 147.18 | 11.54% | 42.31% |
| 5 | 24 | 28 | 30 | 95.47 | 111.38 | 119.33 | 16.66% | 24.99% |
| 6 | 33 | 35 | 35 | 131.27 | 139.22 | 139.22 | 6.06% | 6.06% |
| 7 | 22 | 31 | 30 | 87.51 | 123.31 | 119.33 | 40.91% | 36.36% |
| 8 | 27 | 30 | 31 | 107.4 | 119.33 | 123.11 | 11.11% | 14.63% |
| 9 | 22 | 27 | 26 | 87.51 | 107.4 | 103.42 | 22.73% | 18.18% |
| 10 | 32 | 43 | 39 | 127.29 | 171.04 | 155.13 | 34.37% | 21.87% |
| 11 | 37 | 39 | 35 | 147.18 | 155.13 | 139.22 | 5.40% | −5.41% |
| 12 | 35 | 41 | 36 | 139.22 | 163.09 | 143.2 | 17.15% | 2.86% |
| 13 | 28 | 30 | 38 | 111.38 | 119.33 | 151.15 | 7.14% | 35.71% |
| 14 | 29 | 29 | 29 | 115.35 | 115.35 | 115.35 | 0.00% | 0.00% |
| 15 | 27 | 30 | 31 | 107.4 | 119.33 | 123.31 | 11.11% | 14.81% |
| 16 | 52 | 47 | 48 | 206.84 | 186.95 | 190.93 | −9.62%(*) | −7.69%(*) |
| 17 | 31 | — | — | 123.31 | — | — | — | — |
| 18 | 20 | 34 | 32 | 79.55 | 135.24 | 127.29 | 70.01%(*) | 60.01% |
| 19 | 21 | 22 | 29 | 83.53 | 87.51 | 115.35 | 4.76% | 38.09% |
| 20 | 27 | 27 | 29 | 107.4 | 107.4 | 115.35 | 0.00% | 7.40% |
| | | | | | | | Mean: 14.03% | Mean: 19.27% |

(*)minimal and maximal values, not considered when determining mean of values

In Table 6, more detailed results of hair density and hair density increase of volunteers of group 2:

TABLE 6

| | Nr HAIRS/ 0.25 cm2 | | | HAIR DENSITY 1/cm2 | | | HAIR DENSITY INCREASE | HAIR DENSITY INCREASE |
|---|---|---|---|---|---|---|---|---|
| Voluntary | T0 | T90 | T150 | T0 | T90 | T150 | T90 | T150 |
| 1 | 38 | 45 | 39 | 151.15 | 179 | 155.13 | 18.43% | 2.63% |
| 2 | 33 | 33 | 33 | 131.27 | 131.27 | 131.27 | 0.00% | 0.00% |
| 3 | 29 | 43 | 54 | 115.35 | 171.04 | 214.8 | 48.28% | 86.22%(*) |
| 4 | 26 | 29 | 30 | 103.42 | 115.35 | 119.33 | 11.54% | 15.38% |
| 5 | 26 | 39 | 39 | 103.42 | 155.13 | 155.13 | 50.00% | 50.00% |
| 6 | 38 | 39 | 42 | 151.15 | 155.13 | 167.06 | 2.63% | 10.53% |
| 7 | 23 | 37 | 35 | 91.49 | 147.18 | 139.22 | 60.87%(*) | 52.17% |
| 8 | 21 | 26 | 27 | 83.53 | 103.42 | 107.4 | 23.81% | 28.58% |
| 9 | 33 | 39 | 43 | 131.27 | 155.13 | 171.04 | 18.18% | 30.30% |
| 10 | 31 | — | — | 123.31 | — | — | — | — |
| 11 | 36 | 40 | 41 | 143.2 | 159.11 | 163.09 | 11.11% | 13.89% |
| 12 | 24 | 28 | 27 | 95.47 | 111.38 | 107.4 | 16.66% | 12.50% |
| 13 | 29 | 27 | 30 | 111.35 | 107.4 | 119.33 | 3.55% | 7.17% |
| 14 | 19 | 23 | 19 | 75.58 | 91.49 | 75.58 | 21.05% | 0.00% |
| 15 | 36 | 37 | 34 | 143.2 | 147.8 | 135.24 | 3.21% | −5.56%(*) |
| 16 | 63 | 70 | 61 | 250.6 | 278.44 | 242.64 | 11.11% | −3.18% |
| 17 | 30 | 31 | 32 | 119.33 | 123.31 | 127.29 | 3.34% | 6.67% |
| 18 | 34 | 35 | 34 | 135.24 | 139.22 | 135.24 | 2.94% | 0.00% |
| 19 | 28 | 34 | 42 | 111.38 | 135.24 | 167.06 | 21.42% | 49.99% |
| 20 | 22 | 19 | 26 | 87.57 | 75.58 | 103.42 | −13.69%(*) | 18.10% |
| | | | | | | | Mean: 15.30% | Mean: 17.34% |

(*)minimal and maximal values, not considered when determining mean of values

Figure 8:
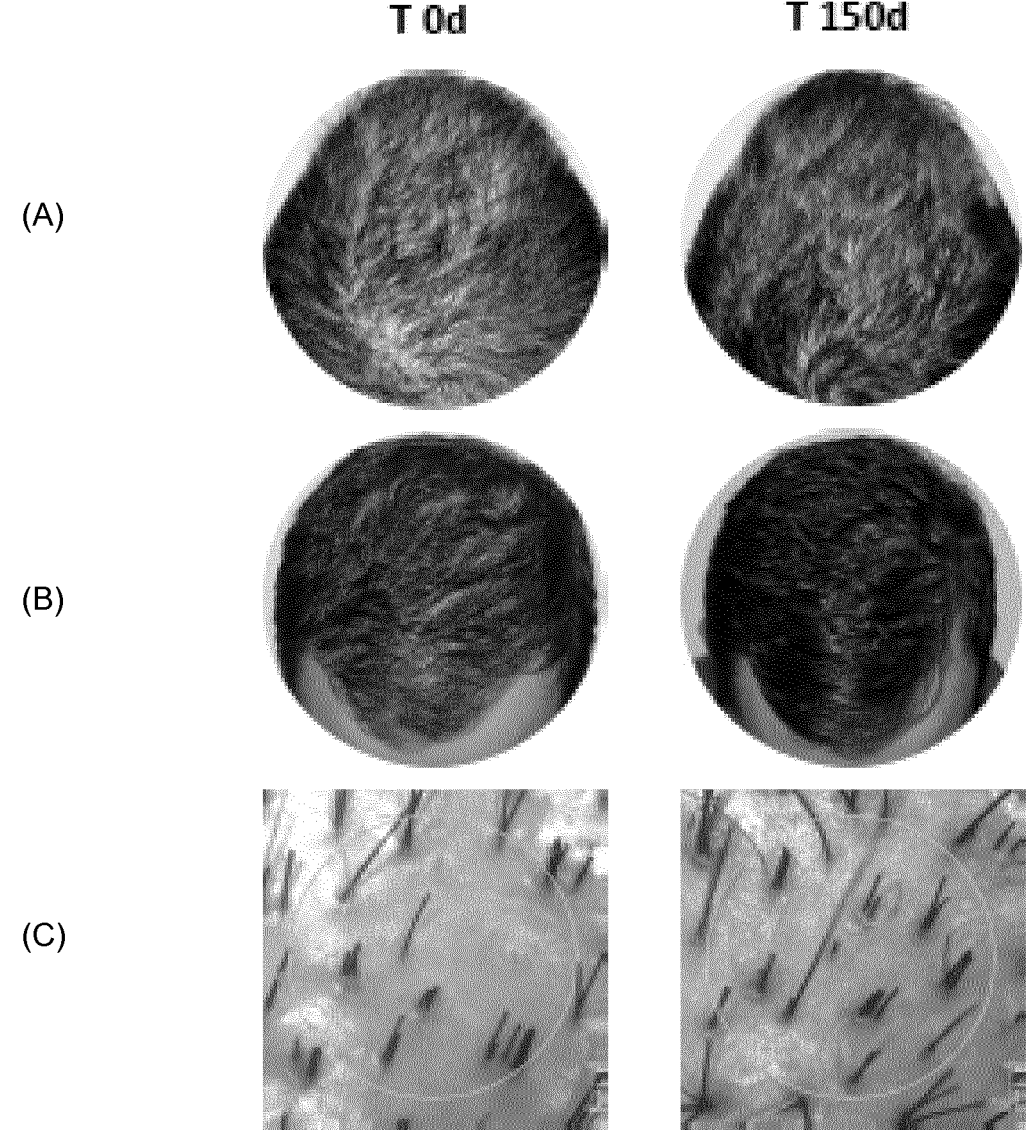
FIG. 8, and FIG. 9, related with Assay 3, depict scalp pictures of occipital (A) and frontal (B) parts, and capillary density microphotographies (C) made with Trichoscan® of volunteers receiving peptide of SEQ ID NO: 6 (FIG. 8), or a cell free supernatant of *Curcuma longa* comprising peptides of formula (I) (FIG. 9).
Figure 9:
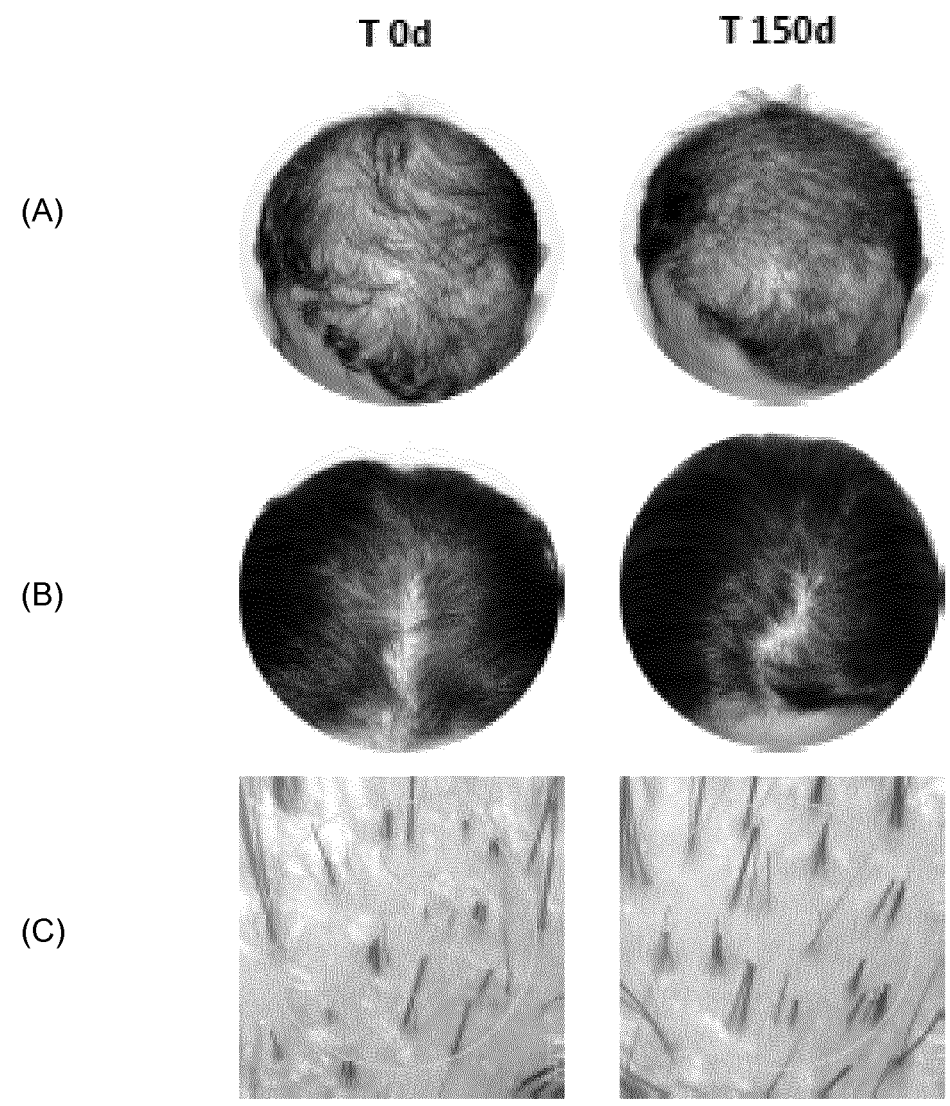

Scalp pictures (frontal and occipital parts), and capillary density by microphotography with Trichoscan® are depicted for a volunteer in group 1 (FIG. 8) and for a volunteer in group 2 (FIG. 9). In both figures (A) and (B) show pictures of occipital and frontal parts, respectively. In (C) the Trichoscan® images.

From all assays on hair density it could be concluded that with a hair density increase of 19.27% (group 1) up to new 14000 hairs appeared in the whole hair. In the same way, with a hair density increase of 17.34% (group 2), up to new 13500 hairs appeared in the whole hair.

Next Table 7 shows the combing test results. In particular, this table includes the average values determined for combing test (number of hair lost during combing). From the combing test results at t=0, t=45 and t=90 the percentage of reduction of hair loss is calculated contrasting values of t=0 with the values at t=45 and at t=90.

TABLE 7

| | % of reduction of hair loss | | |
|---|---|---|---|
| | | % hair-loss reduction | |
| Group | | t = 0 vs t = 45 | t = 0 vs t = 90 |
| 1 (volunteers 1 to 20, males and females) | | 40.48 | 39.72 |
| 2 (volunteers 21 to 40, males and females) | | 52.94 | 56.79 |
| 3 (volunteers 41 to 60, males and females) | | 23.44 | 24.22 |

In Table 8, more detailed results of hair loss of volunteers of group 1:

TABLE 8

| Voluntary | COMBING TEST T0 | COMBING TEST T45 | % REDUCTION OF HAIR LOSS T0 VS. T45 | COMBING TEST T90 | % REDUCTION OF HAIR LOSS T0 VS. T90 | COMBING TEST T150 | % REDUCTION OF HAIR LOSS T0 vs. T150 |
|---|---|---|---|---|---|---|---|
| 1 | 31 | 24 | −22.58 | 23 | −25.81 | 20 | −35.48(*) |
| 2 | 39 | 14 | −64.10 | 22 | −43.59 | 16 | −58.97 |
| 3 | 80 | 46 | −42.50 | 59 | −26.25 | 36 | −55.00 |
| 4 | 69 | 92 | 33.33 | 62 | −10.14 | 20 | −71.01 |
| 5 | 51 | 7 | −86.27 | 6 | −88.24 | 5 | −90.20 |
| 6 | 122 | 54 | −55.74 | 88 | −27.87 | 13 | −89.34 |
| 7 | 43 | 23 | −46.51 | 28 | −34.88 | 13 | −69.77 |
| 8 | 42 | 13 | −69.05 | 28 | −33.33 | 19 | −54.76 |
| 9 | 51 | 88 | 72.55 | 36 | −29.41 | 22 | −56.86 |
| 10 | 65 | 184 | 183.08(*) | 154 | 136.92(*) | 24 | −63.08 |
| 11 | 60 | 34 | −43.33 | 60 | 0.00 | 18 | −70.00 |
| 12 | 104 | 58 | −44.23 | 50 | −51.92 | 12 | −88.46 |
| 13 | 115 | 60 | −47.83 | 61 | −46.96 | 20 | −82.61 |
| 14 | 286 | 62 | −78.32 | 84 | −70.63 | 23 | −91.96(*) |
| 15 | 72 | 50 | −30.56 | 27 | −62.50 | 29 | −59.72 |
| 16 | 535 | 10 | −98.13(*) | 12 | −97.76(*) | 95 | −82.24 |
| 17 | 49 | 31 | −36.73 | — | — | — | — |
| 18 | 89 | 28 | −68.54 | 45 | −49.44 | 19 | −78.65 |
| 19 | 147 | 101 | −31.29 | 118 | −19.73 | 42 | −71.43 |
| 20 | 200 | 66 | −67.00 | 91 | −54.50 | 167 | −16.50 |
| | | | Mean 40.48 | | Mean 39.72 | | Mean 68.15 |

(*)minimal and maximal values, not considered when determining mean of values

In Table 9, more detailed results of hair loss of volunteers of group 2:

TABLE 9

| Voluntary | COMBING TEST T0 | COMBING TEST T45 | % REDUCTION OF HAIR LOSS T0 vs T45 | COMBING TEST T90 | % REDUCTION OF HAIR LOSS T0 vs. T90 | COMBING TEST T150 | % REDUCTION OF HAIR LOSS T0 vs. T150 |
|---|---|---|---|---|---|---|---|
| 21 | 38 | 46 | 21.05(*) | 90 | 136.84(*) | 35 | −7.89 |
| 22 | 41 | 11 | −73.17 | 20 | −51.22 | 37 | −9.76 |
| 23 | 160 | 12 | −92.50(*) | 53 | −66.88 | 26 | −83.75 |
| 24 | 108 | 19 | −82.41 | 31 | −71.30 | 28 | −74.07 |
| 25 | 83 | 75 | −9.64 | 61 | −26.51 | 51 | −38.55 |
| 26 | 82 | 12 | −85.37 | 18 | −78.05 | 9 | −89.02 |
| 27 | 107 | 19 | −82.24 | 11 | −89.72(*) | 16 | −85.05 |
| 28 | 39 | 33 | −15.38 | 21 | −46.15 | 31 | −20.51 |
| 29 | 86 | 35 | −59.30 | 46 | −46.51 | 38 | −55.81 |
| 30 | 67 | — | — | — | — | — | — |
| 31 | 122 | 24 | −80.33 | 19 | −84.43 | 4 | −96.72(*) |
| 32 | 142 | 121 | −14.79 | 99 | −30.28 | 167 | 17.61(*) |
| 33 | 110 | 21 | −80.91 | 22 | −80.00 | 17 | −84.55 |
| 34 | 59 | 27 | −54.24 | 21 | −64.41 | 55 | −6.78 |
| 35 | 54 | 12 | −77.78 | 19 | −64.81 | 23 | −57.41 |
| 36 | 105 | 64 | −39.05 | 45 | −57.14 | 26 | −75.24 |
| 37 | 58 | 58 | 0.00 | 36 | −37.93 | 14 | −75.86 |
| 38 | 92 | 66 | −28.26 | 63 | −31.52 | 43 | −53.26 |

TABLE 9-continued

| Voluntary | COMBING TEST T0 | COMBING TEST T45 | % REDUCTION OF HAIR LOSS T0 vs T45 | COMBING TEST T90 | % REDUCTION OF HAIR LOSS T0 vs. T90 | COMBING TEST T150 | % REDUCTION OF HAIR LOSS T0 vs. T150 |
|---|---|---|---|---|---|---|---|
| 39 | 58 | 23 | −60.34 | 33 | −43.10 | 20 | −65.52 |
| 40 | 81 | 35 | −56.79 | 12.00 | −85.19 | 19.00 | −76.54 |
| | | | Mean 52.94 | | Mean 56.79 | | Mean 56.45 |

(*)minimal and maximal values, not considered when determining mean of values

As derivable from Tables 7 to 9, a meaningful reduction of the % of hair loss was observed when the peptide of SEQ ID NO: 6 or the *Curcuma longa* conditioned media were applied to volunteers. Comparing results at T45, T90 and T150 with t=0 (T0) the percentage of reduction of hair loss was already worthy at T45 and increased with time for the peptide, and maintained after T45 for the *Curcuma longa*.

Assay 4. In Vitro Proliferation Assay to Test the Effect of Fortifying Solutions.

In order to test the effect of a fortifying solution alone, proliferation assays were conducted onto human hair follicle papilla cells (HFDPC), human dermal fibroblasts (HDF) and human immortalized keratinocytes (HaCat).

This fortifying solution is also termed as buffered solution, nutritive solution, or generically as a pharmaceutical, nutraceutical or veterinary composition comprising vitamins, amino acids, and pharmaceutically, nutraceutical or veterinary acceptable salts of iron, magnesium, copper and zinc, together with pharmaceutically, nutraceutical or veterinary acceptable excipients and/or carriers, Thus, one of the buffered solutions assayed was as follows:

500 ml/L of a fortifying solution at 2×

Prepared from (a) a 100× solution, 30 ml/L [wherein the 100× fortifying solution comprised $ZnSO_4 \cdot 5H_2O$ (860 mg/L); 100 μl $CuSO_4 \cdot 5H_2O$ solution (25 g of $CuSO_4 \cdot 5H_2O$ per liter of Fe solution), $MgSO_4 \cdot 5H_2O$ (18054 mg/L), Vitamine C (5000 mg/L), Vitamin B1 (thiamine, 50 mg/L), vitamin B3 (niacin, 50 mg/L), vitamin B5 (D-panthothenate calcium, 50 mg/L), vitamin B6 (pyridoxine, 50 mg/L), glycine (2000 mg/L), methionine (3000 mg/L), phenylalanine (1500 mg/L), proline (3000 mg/L), cysteine (3000 mg/L), glutamic acid (750 mg/L), q.s. of $FeSO_4 \cdot 7H_2O$ solution ($Na_2EDTA \cdot 2H_2O$ (4.46 g/L), $FeSO_4 \cdot 7H_2O$ (3.503 g/L) in miliQ water];

(b) vitamin stock solution 5×, 400 ml/L [wherein the vitamin stick solution 5× is vitamin B2 (riboflavin, 2.5 mg/L), biotin 2.5 mg/L, vitamin B9 (folic acid, 2.5 mg/L) in miliQ water;

(c) an amino acid stock solution 20×, 100 ml/L [wherein the 20× is glutamic acid (450 mg/L), L-phenilalanine (300 mg/L) in miliQ water]

(d) Preservative 1%, 10 ml/L (e) in 1 L of miliQ water.

500 ml/L of phosphate buffered saline (PBS) 2× at pH 6.8

HFDPC, HDF, and the methodology of the assay have been described in the Assays 1 and 2. Human immortalized keratinocytes (HaCat) were obtained from aneuploid immortal keratinocyte cell line from adult human skin . . .

Figure 10:
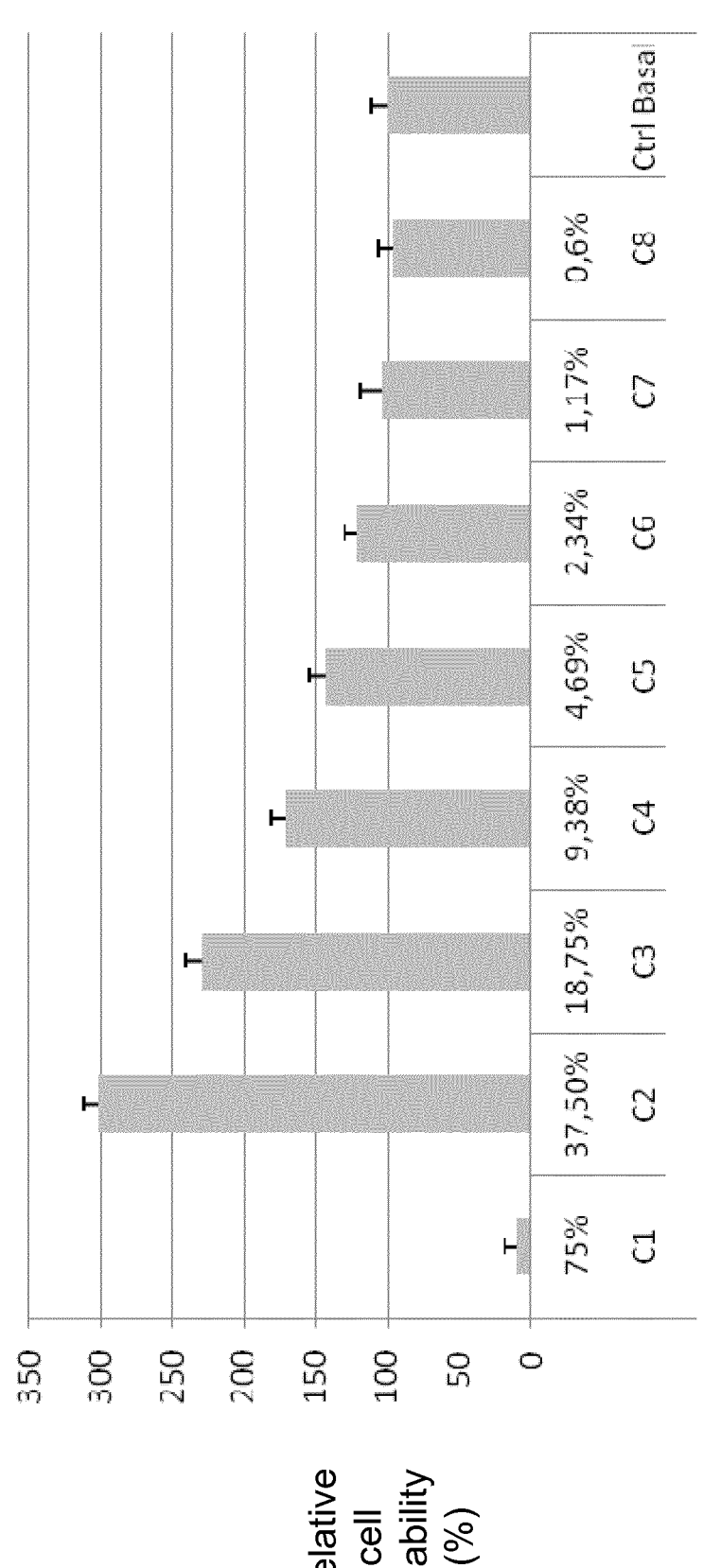
FIG. 10, related with Assay 4, is a graph with the proliferation index (%) of hair follicle dermal papilla cells (HFDPC), when treated with a fortifying composition at different concentrations. "Basal Ctrl" means basal control (non-treated HDFPC), which is accorded a 100% value of proliferation index.
Figure 11:
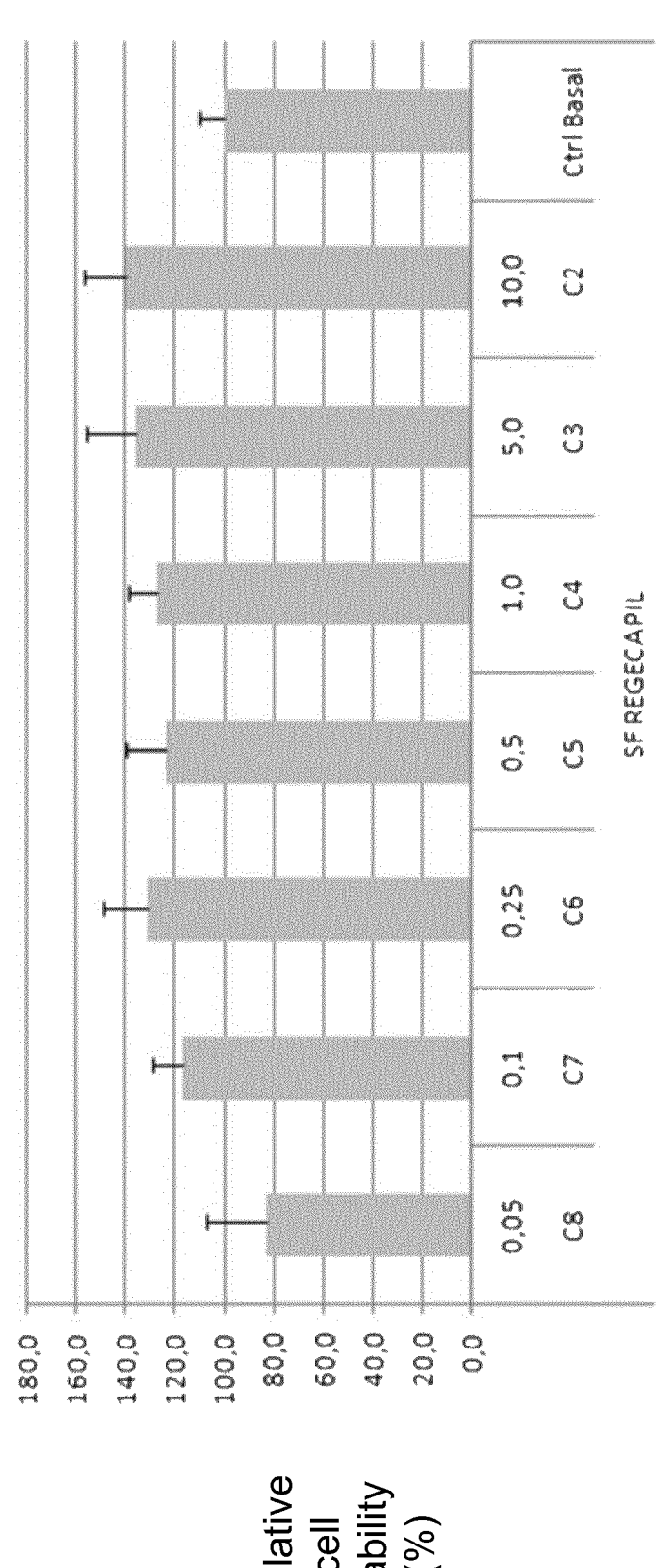
FIG. 11, related with Assay 4, is a graph with the proliferation index (%) of hair dermal fibroblasts (HDF), when treated with a fortifying composition at different concentrations. "Basal Ctrl" means basal control (non-treated HDF), which is accorded a 100% value of proliferation index.
Figure 12:
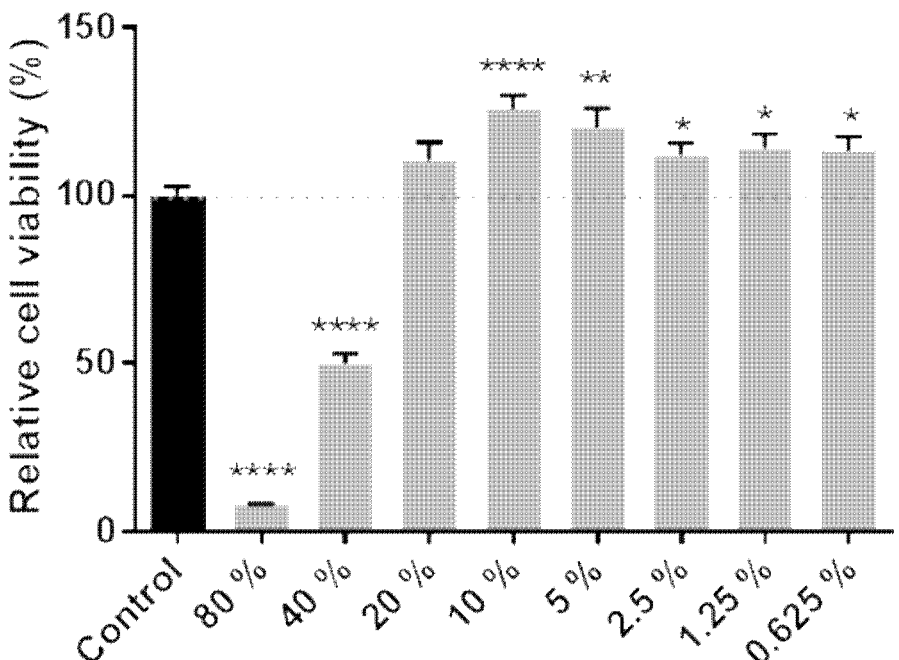
FIG. 12, related with Assay 4, is a graph with the proliferation index (%) of human immortalized keratinocytes (HaCat), when treated with a fortifying composition at different concentrations. "Basal Ctrl" means basal control (non-treated HDFPC), which is accorded a 100% value of proliferation index.

Data are depicted in FIGS. 10, 11 and 12, wherein it is shown the relative cell viability of HFDPC, HDF, and keratinocytes, respectively. The relative cell viability is calculated as the percentage of living cells in relation to the basal control (non-treated cells) which is accorded a 100% value of cell viability.

As observed in the FIG. 10-12, the fortifying solution of the invention promotes the proliferation of the three different cell types, taking as reference or basal control the non-treated cells cultured with media.

It was tested another solution comprising vitamins, amino acids, and pharmaceutically, nutraceutical or veterinary acceptable salts of iron, magnesium, copper and zinc, together with pharmaceutically, nutraceutical or veterinary acceptable excipients and/or carriers. In particular, a composition comprising protein hydrolysate (casein hydrolysate), thiamine, niacin, pantothenic acid, pyridoxine, biotin, folic acid, riboflavin, ascorbic acid, citric acid, myo-inositol, calcium chloride, magnesium sulphate, potassium phosphate, zinc sulphate, copper sulphate, and iron chelate was tested.

Figure 13:
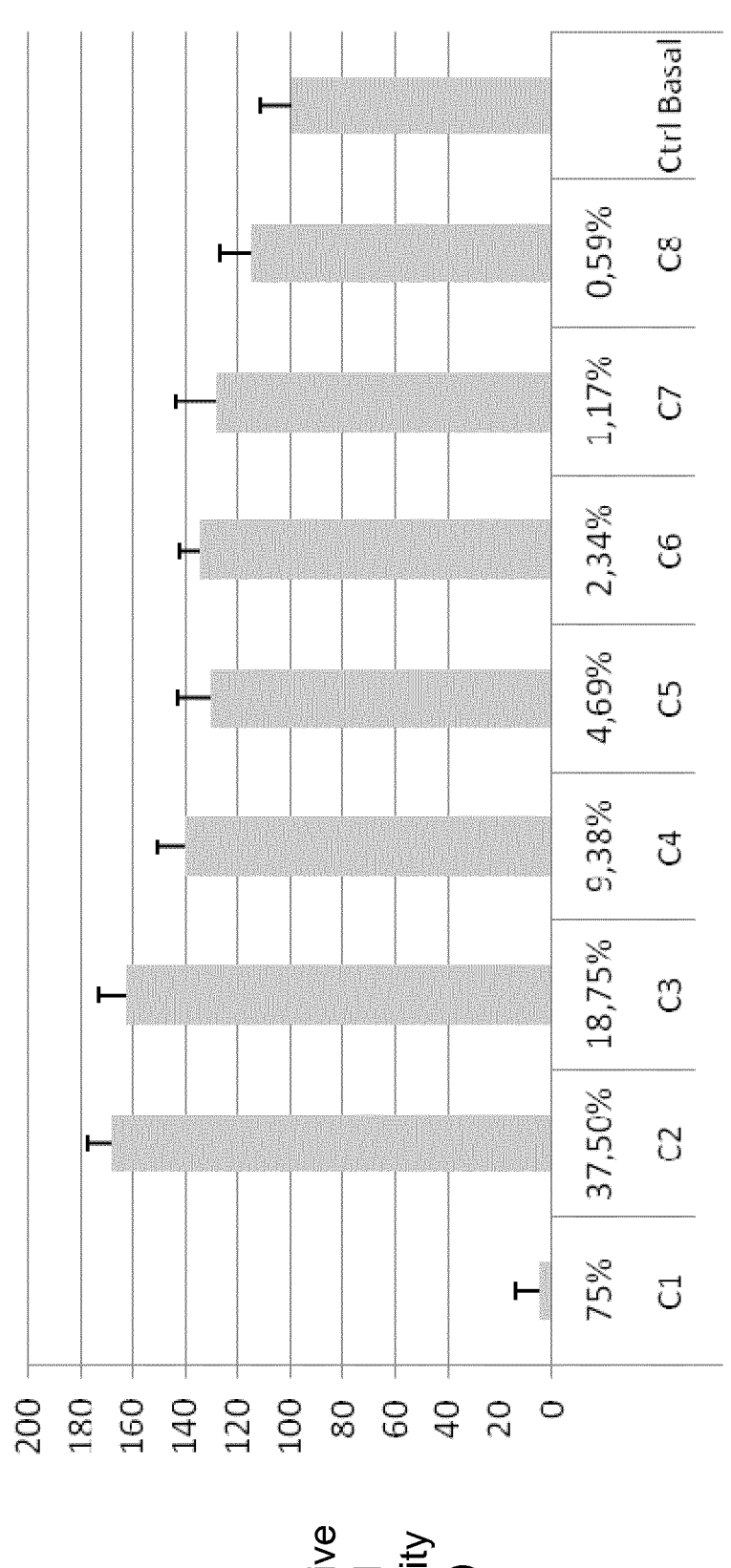
FIG. 13, related with Assay 4, is a graph with the proliferation index (%) of hair follicle dermal papilla cells (HFDPC), when treated with a fortifying composition different of that of FIGS. 10 and 12, at different concentrations. "Basal Ctrl" means basal control (non-treated HDFPC), which is accorded a 100% value of proliferation index.
Figure 14:
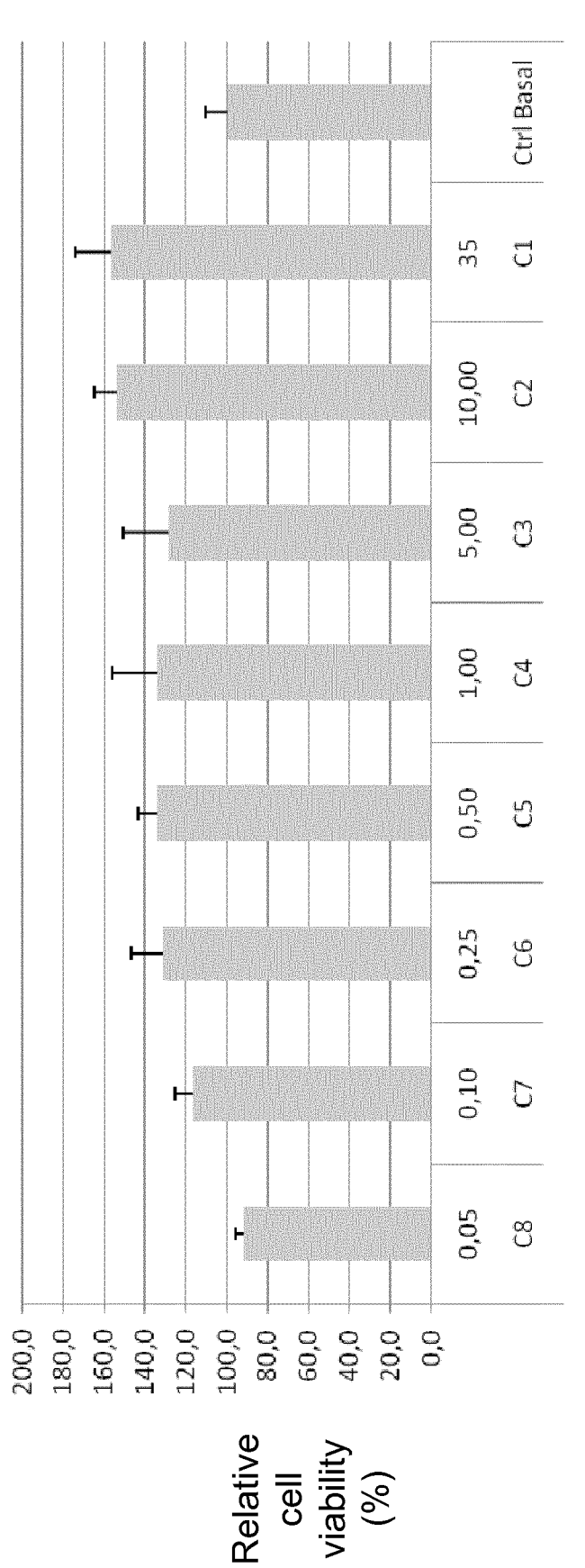
FIG. 14, related with Assay 4, is a graph with the proliferation index (%) of hair dermal fibroblasts (HDF), when treated with the fortifying composition as in FIG. 13 at different concentrations. "Basal Ctrl" means basal control (non-treated HDF), which is accorded a 100% value of proliferation index.
Figure 15:
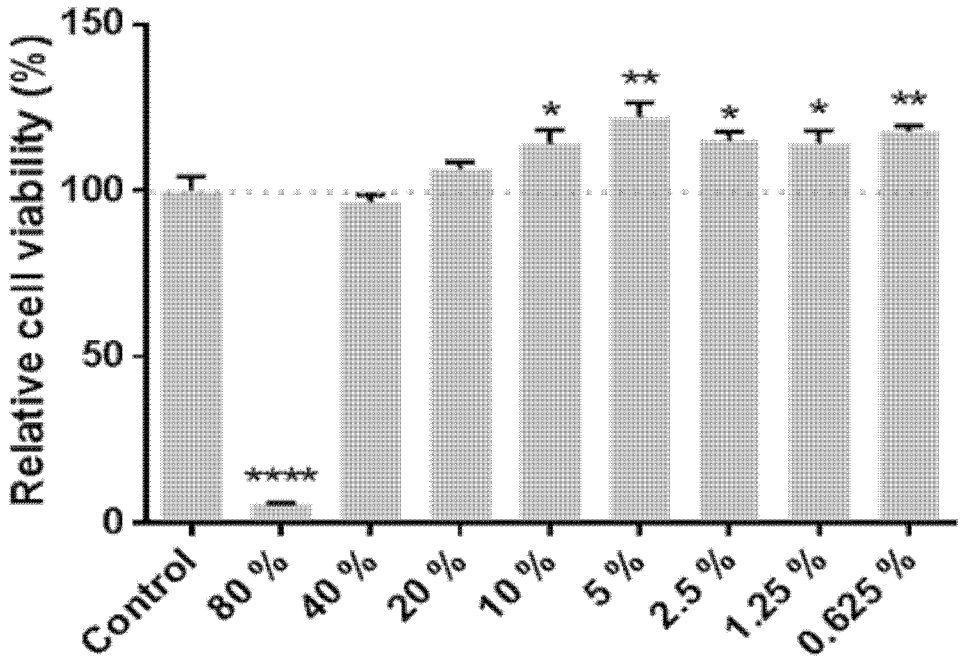
FIG. 15, related with Assay 4, is a graph with the proliferation index (%) of human immortalized keratinocytes (HaCat), when treated with the fortifying composition as in FIG. 13 at different concentrations. "Basal Ctrl" means basal control (non-treated HDFPC), which is accorded a 100% value of proliferation index.

Data are depicted in FIG. 13-15, wherein it is shown the relative cell viability of HFDPC, HDF, and keratinocytes, respectively.

FIG. 13-15 show that this alternative solution also promotes the proliferation of the three different cell types tested, as compared to the non-treated cells.

Both compositions assayed comprised salts of iron, copper, zinc, and magnesium, wherein the weight ratio of iron:copper:zinc:magnesium was from ratio 25:1:30:570 to the ratio 900:1:400:5800. This means that both compositions assayed comprised salts of iron, copper, zinc, and magnesium, wherein the weight ratio of iron to copper was from 25:1 to 900:1, of zinc to copper was from 30:1 to 400:1, and of magnesium to copper was from 570:1 to 5800:1.

In particular, the weight ratio of iron:copper:zinc:magnesium was 868:1:307:5730 in the first solution (that of FIGS. 10-12), and of 25:1:307:2856 in the second solution (of FIGS. 13-15) above described. These weight ratios in this particular examples corresponded to mg of the indicated element (Fe, Cu, Zn and Mg). More in particular they correspond to mg/L in the compositions.

Assay 5. In Vitro Proliferation Assay to Test the Effect of the Peptides of Formula (I) Combined with the Fortifying Solution (Comprising Salts, Vitamins and Amino Acids) of the Invention In order to test whether there was a synergistic effect of the combination of the peptides of the invention and the solutions comprising salts of iron, copper, magnesium and zinc, together with vitamins and amino acids of the invention, proliferation assays were conducted onto human dermal fibroblasts (HDF).

The assayed peptide, the fortifying solution and the culture of HDF have been already described in the previous assays.

Next Table 10 shows tested material and controls:

| Assayed samples |
| --- |
| Basal control (Ctrl): non-treated cells maintained in culture media |
| Peptide 4Aa (CH$_3$—C(O)-YIYT-NH$_2$) (SEQ ID NO: 6) |
| Nutritive Solution: is the fortifying solution as described in Assay 4 with the ratio of iron:copper:zinc:magnesium was 868:1:307:5730. |
| P + NS: Peptide 4Aa and Nutritive Solution used in combination. |

Figure 16:
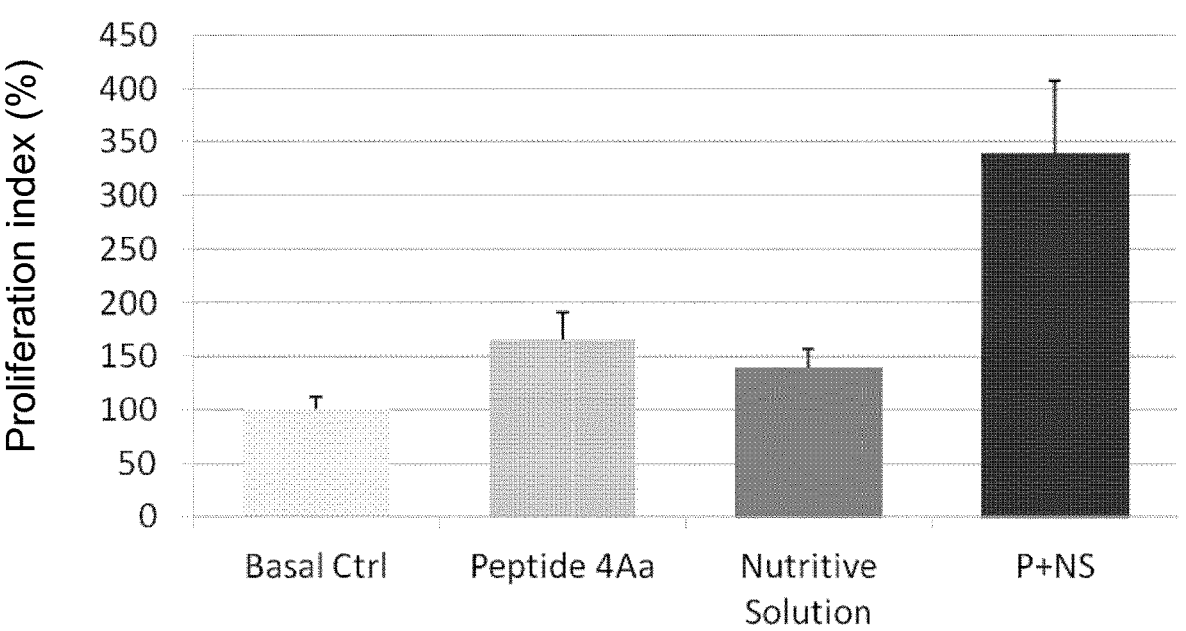
FIG. 16, related with Assay 5, is a graph with the proliferation index (%) of hair follicle dermal papilla cells (HFDPC), when treated with a 4Aa peptide of formula (I), with a fortifying composition, or with a combination of both. "Basal Ctrl" means basal control (non-treated HDFPC), which is accorded a 100% value of proliferation index.

Data are depicted in FIG. 16, wherein it is shown the proliferation index (%) of HDF, calculated as the percentage of growing in relation to the basal control (non-treated HDF) which is accorded a 100% value of proliferation index.

FIG. 16 reveals that both the 4Aa peptide or the fortifying solution alone can promote cell proliferation. Moreover, it is shown that the use of both in combination increases more than two-fold the proliferation of HDF as compared to their use alone. Therefore, it is clear that the use of the peptides and the fortifying solution of the invention in combination elicits a synergistic effect on the proliferation of HDF.

Assay 6. Wound Healing Assay (Reference Example)

In order to test the effect of the sulfaction state of the peptides on their activity, it is herewith provided as reference example a wound healing assay conducted onto human dermal fibroblasts (HDF). The aim of this example is to show that sulfated peptides have the same activity as the non-sulfated peptides.

Next Table 11 shows features of tested products and of controls:

TABLE 11

| Samples assayed in wound healing test Assayed samples |
| --- |
| Basal control (BC) 0.1% Fetal bovine serum (FBS) |
| Positive control (Ctrl+) 10% (FBS) |
| Positive control (Ctrl+) tissular growing factor-β1 (TGF-β1) |
| Peptide 4Aa (SEQ ID NO: 6): 5 µg/ml and 0.05 µg/ml |

32

TABLE 11-continued

| Samples assayed in wound healing test Assayed samples |
| --- |
| Peptide 4AaS1 (SEQ ID NO: 2): 5 µg/ml and 0.05 µg/ml |
| Peptide 4AaS2 (SEQ ID NO: 3): 5 µg/ml and 0.05 µg/ml |

Human dermal fibroblasts were seeded in a 24-well plate and were grown to confluence. A 2 mm width scratch was done on the culture monolayer. Then the test products in culture medium were added and the cicatrisation process was followed by means of phase contrast microscopy. With this aim, photographs were taken at initial of the test (T=0 h) before the scratching and after the treatment (at 12 h and at 72 h). Cicatrisation process was evaluated by quantifying wound area reduction at each time.

Figure 17:
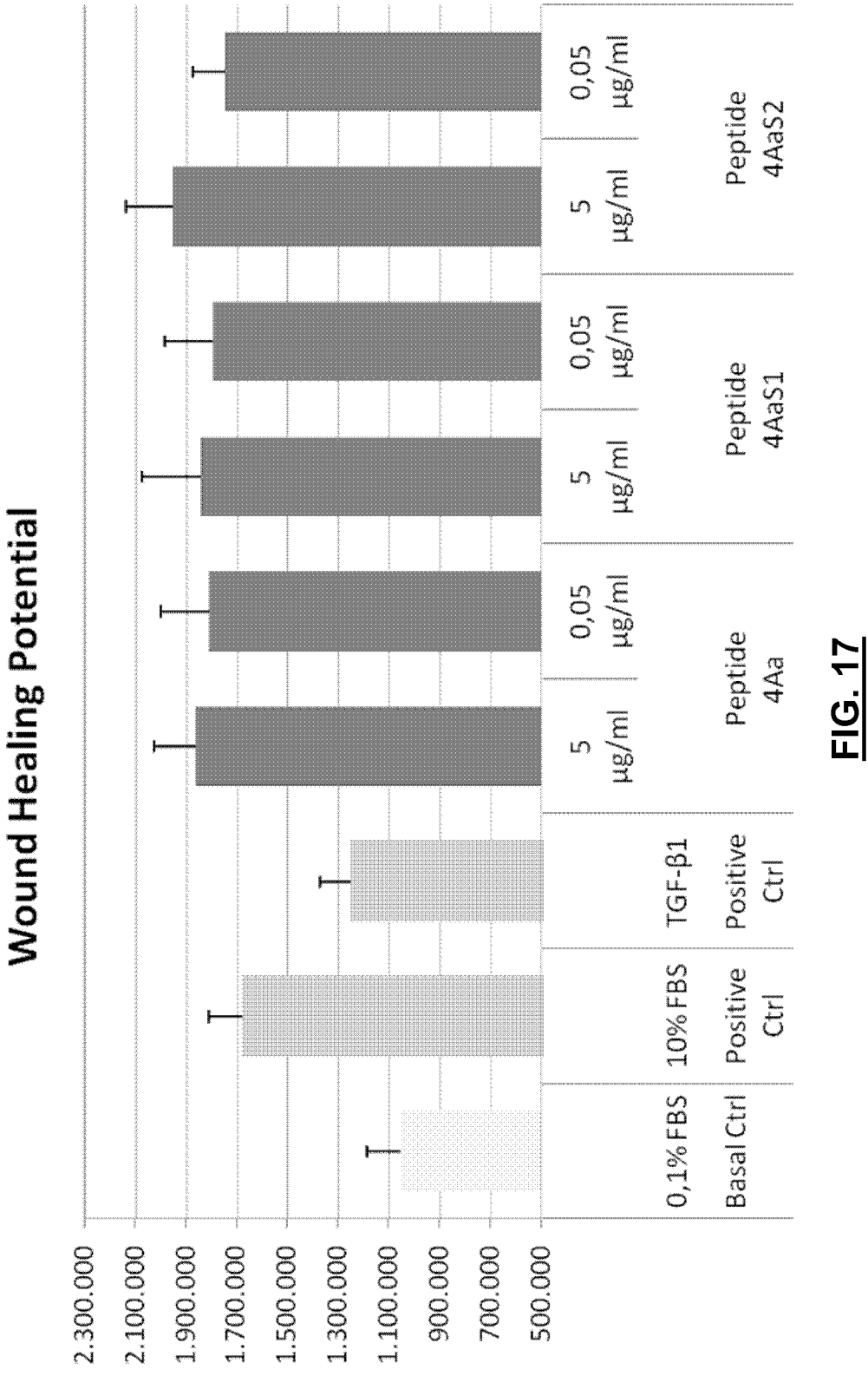
FIG. 17, related with Assay 6 (reference Example), is a graph depicting the wound healing potential of hair dermal fibroblasts (HDF) treated with the peptide 4Aa carrying various sulfation modifications. "Basal Ctrl" means basal control and consists of HDF treated with 0.1% FBS. Two positive controls are represented, either treated with 10% FBS or TGF-β1 (15 ng/ml). The peptide 4AaS1 consists on a modified version of the 4Aa peptide, which carries a —OSO$_3$H radical in the first tyrosine of the peptide (SEQ ID NO: 2); and the peptide 4AaS2 consists on a modified version of the 4Aa peptide, which carries a —OSO$_3$H radical in the second tyrosine of the peptide (SEQ ID NO: 3).

Data at the end of the test (5 days of treatment) are depicted in FIG. 17, wherein the wound healing potential is depicted as the Healed Area (in µm$^2$) for assayed peptide.

The results derive from a triplicate test. Values of cicatrised area (or % of cicatrisation) are the mean values.

From this FIG. 17 it is directly deduced that all tested peptides were more effective than the basal control and they provided effects similar to the positive controls or even higher. This data allow affirming that the peptides are real wound healing promoters.

Furthermore, FIG. 17 reveals that the activity of 4Aa is independent of its sulfaction state, since the 4AaS1 and 4AaS2 sulfated peptides have the same activity as the 4Aa non-sulfated peptide.

REFERENCES CITED IN THE APPLICATION

U.S. Pat. No. 4,139,619
U.S. Pat. No. 4,596,812
U.S. Pat. No. 6,281,241
WO2007113851
WO2006087759
Pumthong et al. "*Curcuma aeruginosa*, a novel botanically derived 5α-reductase inhibitor in the treatment of male-pattern baldness: a multicenter, randomized, double-blind, placebo-controlled study", *Journal of Dermatological Treatment.*—2012; vol. no. 23, pp.: 385-392
Matsubayashi et al., "Phytosulfokine, sulphated peptides that induce the proliferation of single mesophyll cells of Asparagus officinalis L.", *Proc. Natl. Acad. Sci.*—1996, vol. no. 93, pp.: 7623-7627.

SEQUENCE LISTING

```
Sequence total quantity: 19
SEQ ID NO: 1          moltype = AA  length = 5
FEATURE               Location/Qualifiers
source                1..5
                      mol_type = protein
                      organism = synthetic construct
MOD_RES               1
                      note = ACYLATION - Acylated N-terminal tyrosine with R1
                       radical, wherein R1 is a -C(O)-(C1-C20)-alkyl radical
                      note = N-terminal tyrosine with the side-chain hydroxyl
                       group optionally replaced by a radical -OSO3R3; being R3
                       selected from H and (C1-C3)-alkyl
MOD_RES               3
                      note = Tyrosine with the side-chain hydroxyl group
                       optionally replaced by a radical -OSO3R3; being R3
                       selected from H and (C1-C3)-alkyl
MOD_RES               4
                      note = AMIDATION - Amidated C-terminal threonine with a R2
                       radical, when in formula (I) p is 0, and wherein R2 is a
```

-continued

```
                        -NR4R5 radical, being R4 and R5 selected from H, and
                        (C1-C3)-alkyl
MOD_RES                 5
                        note = AMIDATION - Amidated C-terminal glutamine with a R2
                         radical, when in formula (I) p is 1, and wherein R2 is a
                         -NR4R5 radical, being R4 and R5 selected from H, and
                        (C1-C3)-alkyl
SEQUENCE: 1
YIYTQ                                                                     5

SEQ ID NO: 2            moltype = AA   length = 4
FEATURE                 Location/Qualifiers
source                  1..4
                        mol_type = protein
                        organism = synthetic construct
MOD_RES                 1
                        note = ACETYLATION - Acetylated N-terminal Tyrosine
                        note = SULFATATION - Tyrosine (Y) sulphated with a radical
                         -OSO3H
MOD_RES                 4
                        note = AMIDATION - Amidated C-terminal Threonine
SEQUENCE: 2
YIYT                                                                      4

SEQ ID NO: 3            moltype = AA   length = 4
FEATURE                 Location/Qualifiers
MOD_RES                 1
                        note = ACETYLATION - Acetylated N-terminal Tyrosine
MOD_RES                 3
                        note = SULFATATION - Tyrosine (Y) sulphated with a radical
                         -OSO3H.
MOD_RES                 4
                        note = AMIDATION - Amidated C-terminal Threonine
source                  1..4
                        mol_type = protein
                        organism = synthetic construct
SEQUENCE: 3
YIYT                                                                      4

SEQ ID NO: 4            moltype = AA   length = 5
FEATURE                 Location/Qualifiers
MOD_RES                 1
                        note = ACETYLATION - Acetylated N-terminal Tyrosine
MOD_RES                 1
                        note = SULFATATION - Tyrosine (Y) sulphated with a radical
                         -OSO3H
MOD_RES                 5
                        note = AMIDATION - Amidated C-terminal Glutamine
source                  1..5
                        mol_type = protein
                        organism = synthetic construct
SEQUENCE: 4
YIYTQ                                                                     5

SEQ ID NO: 5            moltype = AA   length = 5
FEATURE                 Location/Qualifiers
MOD_RES                 1
                        note = ACETYLATION - Acetylated N-terminal Tyrosine
MOD_RES                 3
                        note = SULFATATION - Tyrosine (Y) sulphated with a radical
                         -OSO3H
MOD_RES                 3
                        note = AMIDATION - Amidated C-terminal Glutamine
source                  1..5
                        mol_type = protein
                        organism = synthetic construct
SEQUENCE: 5
YIYTQ                                                                     5

SEQ ID NO: 6            moltype = AA   length = 4
FEATURE                 Location/Qualifiers
MOD_RES                 1
                        note = ACETYLATION - Acetylated N-terminal Tyrosine
MOD_RES                 4
                        note = AMIDATION - Amidated C-terminal Threonine
source                  1..4
                        mol_type = protein
                        organism = synthetic construct
SEQUENCE: 6
```

```
YIYT                                                                                                     4

SEQ ID NO: 7              moltype = AA  length = 5
FEATURE                   Location/Qualifiers
MOD_RES                   1
                          note = ACETYLATION - Acetylated N-terminal Tyrosine
MOD_RES                   5
                          note = AMIDATION - Amidated C-terminal Glutamine
source                    1..5
                          mol_type = protein
                          organism = synthetic construct
SEQUENCE: 7
YIYTQ                                                                                                    5

SEQ ID NO: 8              moltype = AA  length = 4
FEATURE                   Location/Qualifiers
MOD_RES                   1
                          note = SULFATATION - Tyrosine (Y) sulphated with a radical
                          -OSO3H
source                    1..4
                          mol_type = protein
                          organism = synthetic construct
SEQUENCE: 8
YIYT                                                                                                     4

SEQ ID NO: 9              moltype = AA  length = 4
FEATURE                   Location/Qualifiers
MOD_RES                   3
                          note = SULFATATION - Tyrosine (Y) sulphated with a radical
                          -OSO3H
source                    1..4
                          mol_type = protein
                          organism = synthetic construct
SEQUENCE: 9
YIYT                                                                                                     4

SEQ ID NO: 10             moltype = AA  length = 5
FEATURE                   Location/Qualifiers
REGION                    1..5
                          note = Synthetic peptide
MOD_RES                   1
                          note = SULFATATION - Tyrosine (Y) sulphated with a radical
                          -OSO3H
source                    1..5
                          mol_type = protein
                          organism = synthetic construct
SEQUENCE: 10
YIYTQ                                                                                                    5

SEQ ID NO: 11             moltype = AA  length = 5
FEATURE                   Location/Qualifiers
MOD_RES                   3
                          note = SULFATATION - Tyrosine (Y) sulphated with a radical
                          -OSO3H
source                    1..5
                          mol_type = protein
                          organism = synthetic construct
SEQUENCE: 11
YIYTQ                                                                                                    5

SEQ ID NO: 12             moltype = AA  length = 4
FEATURE                   Location/Qualifiers
source                    1..4
                          mol_type = protein
                          organism = synthetic construct
SEQUENCE: 12
YIYT                                                                                                     4

SEQ ID NO: 13             moltype = AA  length = 5
FEATURE                   Location/Qualifiers
source                    1..5
                          mol_type = protein
                          organism = synthetic construct
SEQUENCE: 13
YIYTQ                                                                                                    5

SEQ ID NO: 14             moltype = AA  length = 4
FEATURE                   Location/Qualifiers
MOD_RES                   1
```

-continued

```
                        note = SULFATATION - Tyrosine (Y) sulphated with a radical
                         -OSO3H
MOD_RES                 3
                        note = SULFATATION - Tyrosine (Y) sulphated with a radical
                         -OSO3H
source                  1..4
                        mol_type = protein
                        organism = synthetic construct
SEQUENCE: 14
YIYT                                                                                     4

SEQ ID NO: 15           moltype = AA   length = 5
FEATURE                 Location/Qualifiers
MOD_RES                 1
                        note = SULFATATION - Tyrosine (Y) sulphated with a radical
                         -OSO3H
MOD_RES                 3
                        note = SULFATATION - Tyrosine (Y) sulphated with a radical
                         -OSO3H
source                  1..5
                        mol_type = protein
                        organism = synthetic construct
SEQUENCE: 15
YIYTQ                                                                                    5

SEQ ID NO: 16           moltype = AA   length = 4
FEATURE                 Location/Qualifiers
MOD_RES                 1
                        note = ACETYLATION - Acetylated N-terminal Tyrosine
source                  1..4
                        mol_type = protein
                        organism = synthetic construct
SEQUENCE: 16
YIYT                                                                                     4

SEQ ID NO: 17           moltype = AA   length = 5
FEATURE                 Location/Qualifiers
MOD_RES                 1
                        note = ACETYLATION - Acetylated N-terminal Tyrosine
source                  1..5
                        mol_type = protein
                        organism = synthetic construct
SEQUENCE: 17
YIYTQ                                                                                    5

SEQ ID NO: 18           moltype = AA   length = 4
FEATURE                 Location/Qualifiers
source                  1..4
                        mol_type = protein
                        organism = synthetic construct
MOD_RES                 4
                        note = AMIDATION - Amidated C-terminal Threonine
SEQUENCE: 18
YIYT                                                                                     4

SEQ ID NO: 19           moltype = AA   length = 5
FEATURE                 Location/Qualifiers
MOD_RES                 5
                        note = AMIDATION - Amidated C-terminal Glutamine
source                  1..5
                        mol_type = protein
                        organism = synthetic construct
SEQUENCE: 19
YIYTQ                                                                                    5
```

The invention claimed is:

1. A method for the treatment of hair loss in a mammal which comprises administering to a mammal in need of such treatment an effective amount of a pharmaceutical, nutraceutical, or veterinary composition comprising a peptide selected from the group consisting of:

```
                                        (SEQ ID NO: 6)
CH3-C(O)-YIYT-NH2;

(SEQ ID NO: 7)
CH3-C(O)-YIYTQ-NH2;

(SEQ ID NO: 12)
YIYT;

(SEQ ID NO: 13)
YIYTQ;

(SEQ ID NO: 16)
CH3-C(O)-YIYT;

(SEQ ID NO: 17)
CH3-C(O)-YIYTQ;

(SEQ ID NO: 18)
YIYT-NH2;

(SEQ ID NO: 19)
YIYTQ-NH2;
``` or a pharmaceutically, nutraceutically, or veterinary acceptable salt thereof;

and mixtures thereof, together with pharmaceutically, nutraceutically, or veterinary acceptable excipients and/or carriers.

2. The method according to claim 1, wherein the peptide is selected from the group consisting of:

```
                                        (SEQ ID NO: 6)
CH3-C(O)-YIYT-NH2;

(SEQ ID NO: 7)
CH3-C(O)-YIYTQ-NH2;
```

-continued

```
                                        (SEQ ID NO: 12)
YIYT;

(SEQ ID NO: 13)
YIYTQ;
``` or a pharmaceutically, nutraceutically, or veterinary acceptable salt thereof;

and mixtures thereof.

3. The method according to claim 1, wherein the pharmaceutical, nutraceutical, or veterinary composition further comprises one or more vitamins, one or more amino acids, and pharmaceutically, nutraceutically, or veterinary acceptable salts of iron, magnesium, copper and zinc.

4. The method according to claim 3, wherein the one or more vitamins are selected from the group consisting of vitamin C, vitamin B1, vitamin B3, vitamin B5, vitamin B6, vitamin B2, vitamin B8, vitamin B9, and mixtures thereof.

5. The method according to claim 3, wherein the one or more amino acids are selected from the group consisting of glutamic acid, phenylalanine, glycine, methionine, proline, cysteine and mixtures thereof.

6. The method according to claim 3, wherein the weight ratio of iron to copper is from 25:1 to 900:1, of zinc to copper is from 30:1 to 400:1, and of magnesium to copper is from 570:1 to 5800:1.

7. The method according to claim 3, wherein the pharmaceutically, nutraceutically, or veterinary acceptable salts of iron, magnesium, copper and zinc are inorganic salts selected from the group consisting of iron sulphate, copper sulphate, zinc sulphate, magnesium sulphate, and mixtures thereof.

8. The method according to claim 1, wherein the pharmaceutical, nutraceutical, or veterinary composition further comprises vitamin C, vitamin B1, vitamin B2, vitamin B3, vitamin B5, vitamin B6, vitamin B8, vitamin B9, glycine, methionine, phenylalanine, proline, cysteine, glutamic acid, zinc sulphate, copper sulphate, magnesium sulphate and iron sulphate together with pharmaceutically, nutraceutically or veterinary acceptable excipients and/or carriers.

* * * * *